US012712087B2

(12) United States Patent
Durkin et al.

(10) Patent No.: US 12,712,087 B2
(45) Date of Patent: Aug. 18, 2026

(54) SYSTEMS AND METHODS FOR GENE VARIANT GROUPING AND VISUALIZATION

(71) Applicant: Genomenon, Inc., Ann Arbor, MI (US)

(72) Inventors: Daniel Durkin, Burlington, CT (US); Sara Patterson, Old Lyme, CT (US); Maksym Tashchuk, South Windsor, CT (US); Cara Statz, Farmington, CT (US); Taofei Yin, West Hartford, CT (US); Tushar Deshpande, Farmington, CT (US); Asha Thadikemalla, Farmington, CT (US); Ryan Russell, Prospect, CT (US); Gopinath Rajadinakaran, Milford, CT (US); Susan Mockus, Cherry Log, GA (US)

(73) Assignee: Genomenon, Inc., Ann Arbor, MI (US)

( * ) Notice: Subject to any disclaimer, the term of this patent is extended or adjusted under 35 U.S.C. 154(b) by 895 days.

(21) Appl. No.: 17/917,751

(22) PCT Filed: Apr. 9, 2021

(86) PCT No.: PCT/US2021/026625

§ 371 (c)(1),
(2) Date: Oct. 7, 2022

(87) PCT Pub. No.: WO2021/207631

PCT Pub. Date: Oct. 14, 2021

(65) Prior Publication Data

US 2023/0298769 A1 Sep. 21, 2023

Related U.S. Application Data

(60) Provisional application No. 63/008,222, filed on Apr. 10, 2020.

(51) Int. Cl.
*G16H 70/60* (2018.01)
*G16B 20/00* (2019.01)
(Continued)

(52) U.S. Cl.
CPC ............ *G16H 70/60* (2018.01); *G16B 20/00* (2019.02); *G16B 40/00* (2019.02); *G16B 50/10* (2019.02); *G16H 50/30* (2018.01)

(58) Field of Classification Search
CPC ........ G16H 70/60; G16H 50/30; G16B 40/00; G16B 50/10; G16B 20/00
See application file for complete search history.

(56) References Cited

U.S. PATENT DOCUMENTS 6,056,690 A * 5/2000 Roberts ................ G06F 18/256 128/920
6,389,308 B1 * 5/2002 Shusterman .......... A61B 5/349 600/509

(Continued)

OTHER PUBLICATIONS

Mougin, Elsevier, 2017, pp. 3-18.*

(Continued)

*Primary Examiner* — Michael I Ezewoko
(74) *Attorney, Agent, or Firm* — Wolf, Greenfield & Sacks, P.C.

(57) ABSTRACT

Genetic variations associated with a patient's cancerous tumors can be indicative of potential effective treatments for treating the patient. Systems and methods for determining relationships between gene variants of a gene, the gene variants being related to one or more cancers and being correlated to a treatment response of the one or more cancers to one or more medications, are provided. The method includes accessing, using at least one processor, a database comprising information about the gene variants, the information including at least information indicative of a treatment response of a first gene variant of the gene variants to one or more treatments; categorizing the information about the gene variants within a plurality of groups; and generating hierarchical relationships between each group of the plurality of groups. In some embodiments, a patient may be treated (Continued)

using a treatment selected based on the generated hierarchical relationships.

18 Claims, 25 Drawing Sheets

(51) Int. Cl.

| | |
|---|---|
| ***G16B 40/00*** | (2019.01) |
| ***G16B 50/10*** | (2019.01) |
| ***G16H 50/30*** | (2018.01) |

(56) References Cited

U.S. PATENT DOCUMENTS

| | | | | |
|---|---|---|---|---|
| 6,897,875 | B2 * | 5/2005 | Zhang | G16B 45/00 345/589 |
| 8,838,506 | B2 * | 9/2014 | Glaser-Seidnitzer | G16H 70/20 706/12 |
| 8,879,813 | B1 * | 11/2014 | Solanki | G06T 5/94 382/128 |
| 10,586,612 | B2 * | 3/2020 | Ury | G16H 40/67 |
| 10,878,064 | B2 * | 12/2020 | Burns | G16H 10/20 |
| 11,302,443 | B2 * | 4/2022 | Kartoun | G16H 20/10 |
| 11,556,522 | B2 * | 1/2023 | Fry | G06F 16/2246 |
| 11,567,918 | B2 * | 1/2023 | Jayakumar | G06F 16/2428 |
| 11,568,957 | B2 * | 1/2023 | Reid | G16B 20/00 |
| 11,588,630 | B1 * | 2/2023 | Neumann | H04L 9/3231 |
| 11,651,442 | B2 * | 5/2023 | Colley | G06Q 40/08 705/2 |
| 11,681,917 | B2 * | 6/2023 | Xiong | G06N 3/084 706/25 |
| 11,682,481 | B2 * | 6/2023 | Lefkofsky | G16B 20/00 705/2 |
| 11,773,449 | B2 * | 10/2023 | Tabori | A61P 35/00 514/789 |
| 11,842,802 | B2 * | 12/2023 | Mao | G16H 10/20 |
| 11,860,941 | B2 * | 1/2024 | Kloke | G06F 16/9024 |
| 11,875,901 | B2 * | 1/2024 | Lei | G16H 50/70 |
| 11,887,696 | B2 * | 1/2024 | Frey | G16B 20/20 |
| 11,895,235 | B1 * | 2/2024 | Neumann | H04L 9/3247 |
| 11,978,531 | B2 * | 5/2024 | Zaaijer | G16B 30/00 |
| 12,013,863 | B2 * | 6/2024 | Leighton | G16B 40/00 |
| 12,014,281 | B2 * | 6/2024 | Dehan | G16B 20/20 |
| 12,071,669 | B2 * | 8/2024 | Maxwell | G16B 30/00 |
| 12,191,002 | B2 * | 1/2025 | Dalchau | G16B 40/10 |
| 12,260,945 | B2 * | 3/2025 | Casale | G16H 20/10 |
| 2003/0142094 | A1 * | 7/2003 | Zhang | G16B 40/30 345/440 |
| 2009/0105167 | A1 * | 4/2009 | Potti | A61K 31/7048 506/17 |
| 2012/0239671 | A1 * | 9/2012 | Chaudhri | G16H 50/70 707/756 |
| 2013/0238351 | A1 * | 9/2013 | Burns | G16H 10/20 705/2 |
| 2013/0296175 | A1 | 11/2013 | Rafnar et al. | |
| 2014/0359422 | A1 * | 12/2014 | Bassett, Jr. | G16B 20/00 707/754 |
| 2015/0046191 | A1 * | 2/2015 | Futscher de Deus | G16H 10/60 705/3 |
| 2015/0081323 | A1 * | 3/2015 | Jackson | G16B 20/20 705/2 |
| 2015/0248525 | A1 * | 9/2015 | Ury | G06F 16/245 705/3 |
| 2015/0363559 | A1 * | 12/2015 | Jackson | G16B 20/20 705/2 |
| 2015/0379193 | A1 * | 12/2015 | Bassett, Jr. | G16B 20/00 702/19 |
| 2016/0092631 | A1 * | 3/2016 | Yandell | G16B 50/10 702/19 |
| 2017/0076046 | A1 * | 3/2017 | Barnes | G06Q 10/06 |
| 2017/0124415 | A1 * | 5/2017 | Choi | G06N 3/08 |
| 2017/0159130 | A1 * | 6/2017 | Mitra | C12Q 1/6886 |
| 2017/0316183 | A1 * | 11/2017 | Burns | G16H 10/20 |
| 2018/0276340 | A1 * | 9/2018 | Dutkowski | A61K 9/2013 |
| 2019/0087538 | A1 * | 3/2019 | Lim | A61P 35/00 |
| 2019/0220572 | A1 * | 7/2019 | Levovitz | G16B 45/00 |
| 2019/0259474 | A1 * | 8/2019 | Wang | G16B 40/20 |
| 2019/0370965 | A1 * | 12/2019 | Lay | G06N 20/00 |
| 2020/0020430 | A1 * | 1/2020 | Futscher de Deus | G16H 20/10 |
| 2020/0273572 | A1 * | 8/2020 | Kartoun | G06F 40/30 |
| 2020/0286622 | A1 * | 9/2020 | Jung | G16B 20/00 |
| 2020/0327962 | A1 * | 10/2020 | Chittenden | G16B 40/20 |
| 2021/0012882 | A1 * | 1/2021 | Lefkofsky | G16B 20/00 |
| 2021/0073352 | A9 * | 3/2021 | Dutkowski | G16B 5/00 |
| 2021/0183524 | A1 * | 6/2021 | Lee | G16B 50/10 |
| 2022/0181029 | A1 * | 6/2022 | Colley | G06Q 40/08 |
| 2022/0261668 | A1 * | 8/2022 | Stumpe | G06F 16/24578 |
| 2022/0392570 | A1 * | 12/2022 | Murphy | G16B 20/20 |
| 2023/0050513 | A1 * | 2/2023 | Morganella | G16B 45/00 |
| 2023/0068937 | A1 * | 3/2023 | Morganella | G16B 40/20 |
| 2023/0298769 | A1 * | 9/2023 | Durkin | G16H 50/30 705/2 |
| 2023/0386643 | A1 * | 11/2023 | Lefkofsky | G16H 20/70 |
| 2024/0037740 | A1 * | 2/2024 | Jha | G06V 10/267 |
| 2024/0274254 | A1 * | 8/2024 | Casale | G16H 50/50 |
| 2024/0404700 | A1 * | 12/2024 | Trakadis | G16H 20/00 |
| 2024/0412878 | A1 * | 12/2024 | Krakow | G06F 9/451 |
| 2025/0037823 | A1 * | 1/2025 | Erbach | G16H 10/60 |
| 2025/0201341 | A1 * | 6/2025 | Kearns | G16B 20/00 |
| 2025/0273294 | A1 * | 8/2025 | Cui | G16B 20/20 |

OTHER PUBLICATIONS

Shehu, Springer, 2016, pp. 225-298.*

Kuo, Elsevier, Jan. 2020, pp. 1-12.*

International Search Report and Written Opinion for International Application No. PCT/US2021/026625, mailed Jul. 22, 2021.

International Preliminary Report on Patentability for International Application No. PCT/US2021/026625, mailed Oct. 20, 2022.

PCT/US2021/026625, Jul. 22, 2021, International Search Report and Written Opinion.

PCT/US2021/026625, Oct. 20, 2022, International Preliminary Report on Patentability.

* cited by examiner

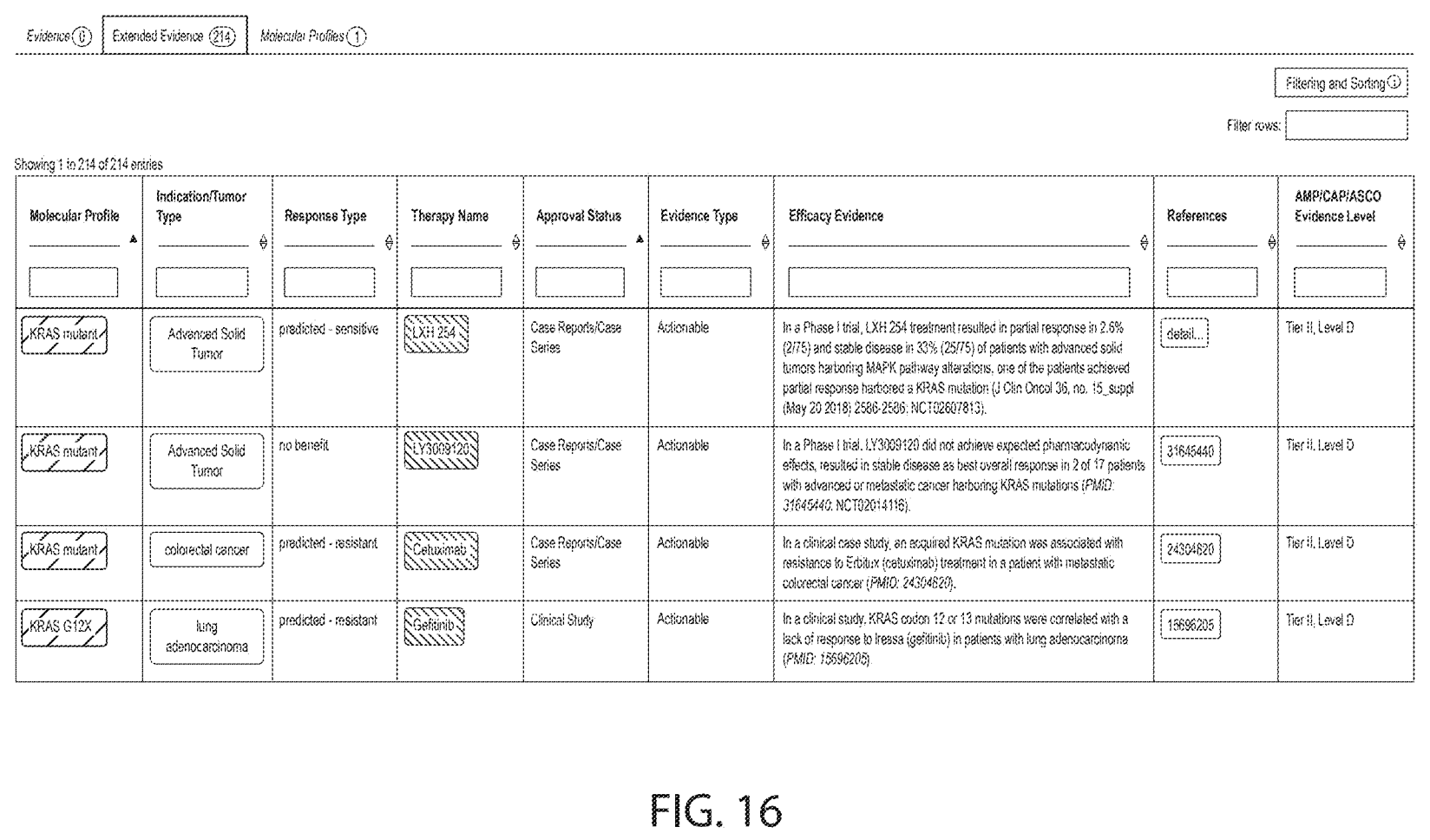

Evidence (6) | Extended Evidence (214) | Molecular Profiles (1)

Filtering and Sorting

Filter rows:

Showing 1 to 214 of 214 entries

| Molecular Profile | Indication/Tumor Type | Response Type | Therapy Name | Approval Status | Evidence Type | Efficacy Evidence | References | AMP/CAP/ASCO Evidence Level |
|---|---|---|---|---|---|---|---|---|
| KRAS mutant | Advanced Solid Tumor | predicted - sensitive | LXH 254 | Case Reports/Case Series | Actionable | In a Phase I trial, LXH 254 treatment resulted in partial response in 2.6% (2/75) and stable disease in 33% (25/75) of patients with advanced solid tumors harboring MAPK pathway alterations, one of the patients achieved partial response harbored a KRAS mutation (J Clin Oncol 36, no. 15_suppl (May 20 2018) 2586-2586; NCT02607813). | detail... | Tier II, Level D |
| KRAS mutant | Advanced Solid Tumor | no benefit | LY3009120 | Case Reports/Case Series | Actionable | In a Phase I trial, LY3009120 did not achieve expected pharmacodynamic effects, resulted in stable disease as best overall response in 2 of 17 patients with advanced or metastatic cancer harboring KRAS mutations (*PMID: 31645440*; NCT02014116). | 31645440 | Tier II, Level D |
| KRAS mutant | colorectal cancer | predicted - resistant | Cetuximab | Case Reports/Case Series | Actionable | In a clinical case study, an acquired KRAS mutation was associated with resistance to Erbitux (cetuximab) treatment in a patient with metastatic colorectal cancer (*PMID: 24304620*). | 24304620 | Tier II, Level D |
| KRAS G12X | lung adenocarcinoma | predicted - resistant | Gefitinib | Clinical Study | Actionable | In a clinical study, KRAS codon 12 or 13 mutations were correlated with a lack of response to Iressa (gefitinib) in patients with lung adenocarcinoma (*PMID: 15696205*) | 15696205 | Tier II, Level D |

FIG. 16

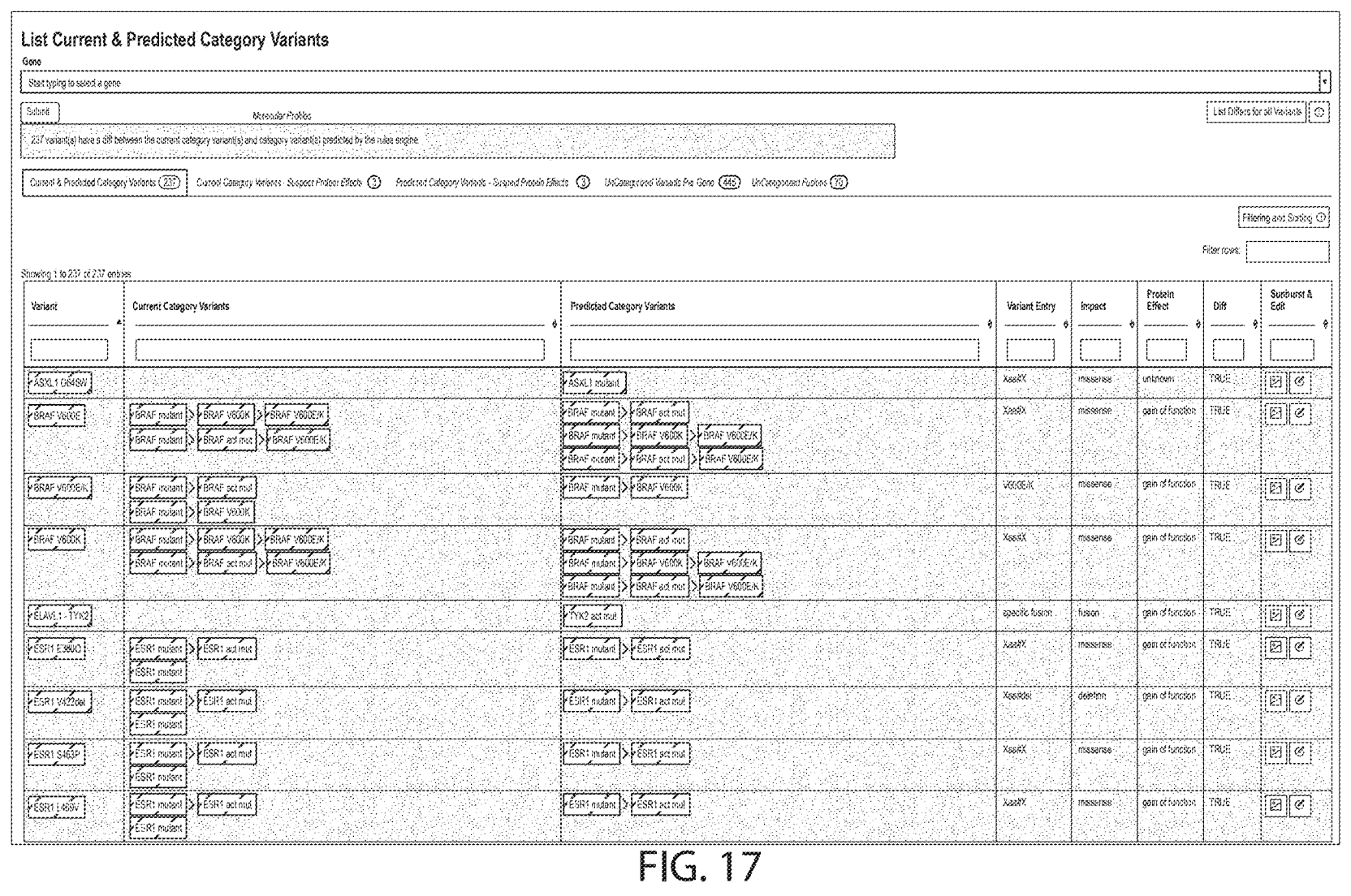

List Current & Predicted Category Variants

Gene

Start typing to select a gene

Submit

Molecular Profiles 237 variant(s) have a diff between the current category variant(s) and category variant(s) predicted by the rules engine.

List Diffs for all Variants

Current & Predicted Category Variants (237) | Current Category Variants - Suspect Protein Effects (3) | Predicted Category Variants - Suspect Protein Effects (3) | UnCategorized Variants Per Gene (446) | UnCategorized Fusions (70)

Filtering and Sorting

Filter rows:

Showing 1 to 237 of 237 entries

| Variant | Current Category Variants | Predicted Category Variants | Variant Entry | Impact | Protein Effect | Diff | Sunburst & Edit |
|---|---|---|---|---|---|---|---|
| ASXL1 G646W | | ASXL1 mutant | Xaa#X | missense | unknown | TRUE | |
| BRAF V600E | BRAF mutant > BRAF V600K > BRAF V600E/K<br>BRAF mutant > BRAF act mut > BRAF V600E/K | BRAF mutant > BRAF act mut<br>BRAF mutant > BRAF V600K > BRAF V600E/K<br>BRAF mutant > BRAF act mut > BRAF V600E/K | Xaa#X | missense | gain of function | TRUE | |
| BRAF V600E/K | BRAF mutant > BRAF act mut<br>BRAF mutant > BRAF V600K | BRAF mutant > BRAF V600K | V600E/K | missense | gain of function | TRUE | |
| BRAF V600K | BRAF mutant > BRAF V600K > BRAF V600E/K<br>BRAF mutant > BRAF act mut > BRAF V600E/K | BRAF mutant > BRAF act mut<br>BRAF mutant > BRAF V600K > BRAF V600E/K<br>BRAF mutant > BRAF act mut > BRAF V600E/K | Xaa#X | missense | gain of function | TRUE | |
| ELAVL1 - TYK2 | | TYK2 act mut | specific fusion | fusion | gain of function | TRUE | |
| ESR1 E380Q | ESR1 mutant > ESR1 act mut<br>ESR1 mutant | ESR1 mutant > ESR1 act mut | Xaa#X | missense | gain of function | TRUE | |
| ESR1 V422del | ESR1 mutant > ESR1 act mut<br>ESR1 mutant | ESR1 mutant > ESR1 act mut | Xaa#del | deletion | gain of function | TRUE | |
| ESR1 S463P | ESR1 mutant > ESR1 act mut<br>ESR1 mutant | ESR1 mutant > ESR1 act mut | Xaa#X | missense | gain of function | TRUE | |
| ESR1 L469V | ESR1 mutant > ESR1 act mut<br>ESR1 mutant | ESR1 mutant > ESR1 act mut | Xaa#X | missense | gain of function | TRUE | |

FIG. 17

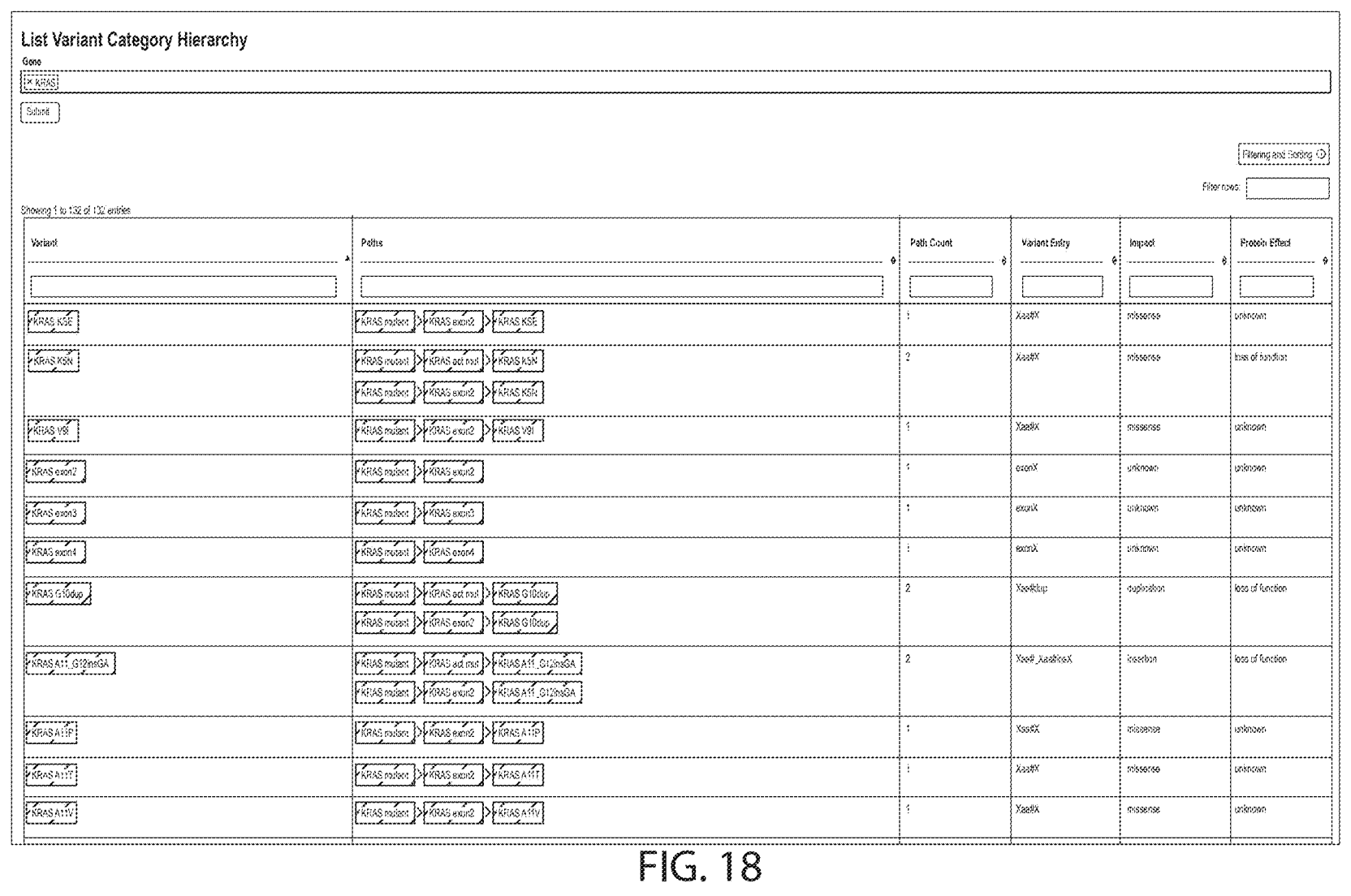

List Variant Category Hierarchy

Gene

× KRAS

Submit

Filtering and Sorting

Filter rows:

Showing 1 to 132 of 132 entries

| Variant | Paths | Path Count | Variant Entry | Impact | Protein Effect |
|---|---|---|---|---|---|
| KRAS K5E | KRAS mutant > KRAS exon2 > KRAS K5E | 1 | Xaa#X | missense | unknown |
| KRAS K5N | KRAS mutant > KRAS act mut > KRAS K5N<br>KRAS mutant > KRAS exon2 > KRAS K5N | 2 | Xaa#X | missense | loss of function |
| KRAS V9I | KRAS mutant > KRAS exon2 > KRAS V9I | 1 | Xaa#X | missense | unknown |
| KRAS exon2 | KRAS mutant > KRAS exon2 | 1 | exonX | unknown | unknown |
| KRAS exon3 | KRAS mutant > KRAS exon3 | 1 | exonX | unknown | unknown |
| KRAS exon4 | KRAS mutant > KRAS exon4 | 1 | exonX | unknown | unknown |
| KRAS G10dup | KRAS mutant > KRAS act mut > KRAS G10dup<br>KRAS mutant > KRAS exon2 > KRAS G10dup | 2 | Xaa#dup | duplication | loss of function |
| KRAS A11_G12insGA | KRAS mutant > KRAS act mut > KRAS A11_G12insGA<br>KRAS mutant > KRAS exon2 > KRAS A11_G12insGA | 2 | Xaa#_Xaa#insX | insertion | loss of function |
| KRAS A11P | KRAS mutant > KRAS exon2 > KRAS A11P | 1 | Xaa#X | missense | unknown |
| KRAS A11T | KRAS mutant > KRAS exon2 > KRAS A11T | 1 | Xaa#X | missense | unknown |
| KRAS A11V | KRAS mutant > KRAS exon2 > KRAS A11V | 1 | Xaa#X | missense | unknown |

FIG. 18

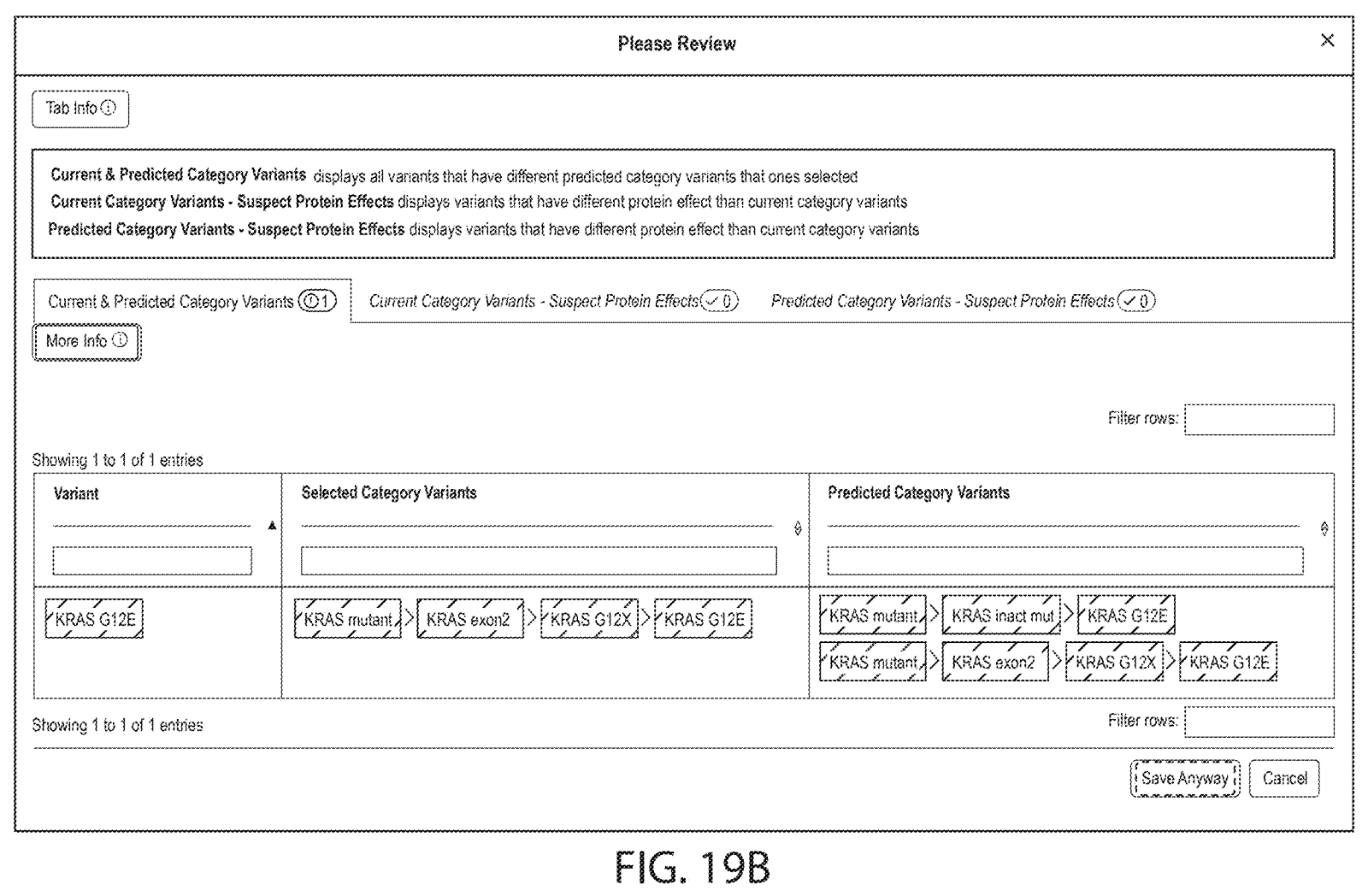

Please Review

×

Tab Info ⓘ

Current & Predicted Category Variants displays all variants that have different predicted category variants that ones selected
Current Category Variants - Suspect Protein Effects displays variants that have different protein effect than current category variants
Predicted Category Variants - Suspect Protein Effects displays variants that have different protein effect than current category variants Current & Predicted Category Variants ⓘ1 *Current Category Variants - Suspect Protein Effects* ✓0 *Predicted Category Variants - Suspect Protein Effects* ✓0

More Info ⓘ

Filter rows:

Showing 1 to 1 of 1 entries

| Variant | Selected Category Variants | Predicted Category Variants |
|---|---|---|
| KRAS G12E | KRAS mutant > KRAS exon2 > KRAS G12X > KRAS G12E | KRAS mutant > KRAS inact mut > KRAS G12E<br>KRAS mutant > KRAS exon2 > KRAS G12X > KRAS G12E |

Showing 1 to 1 of 1 entries

Filter rows:

Save Anyway

Cancel

FIG. 19B

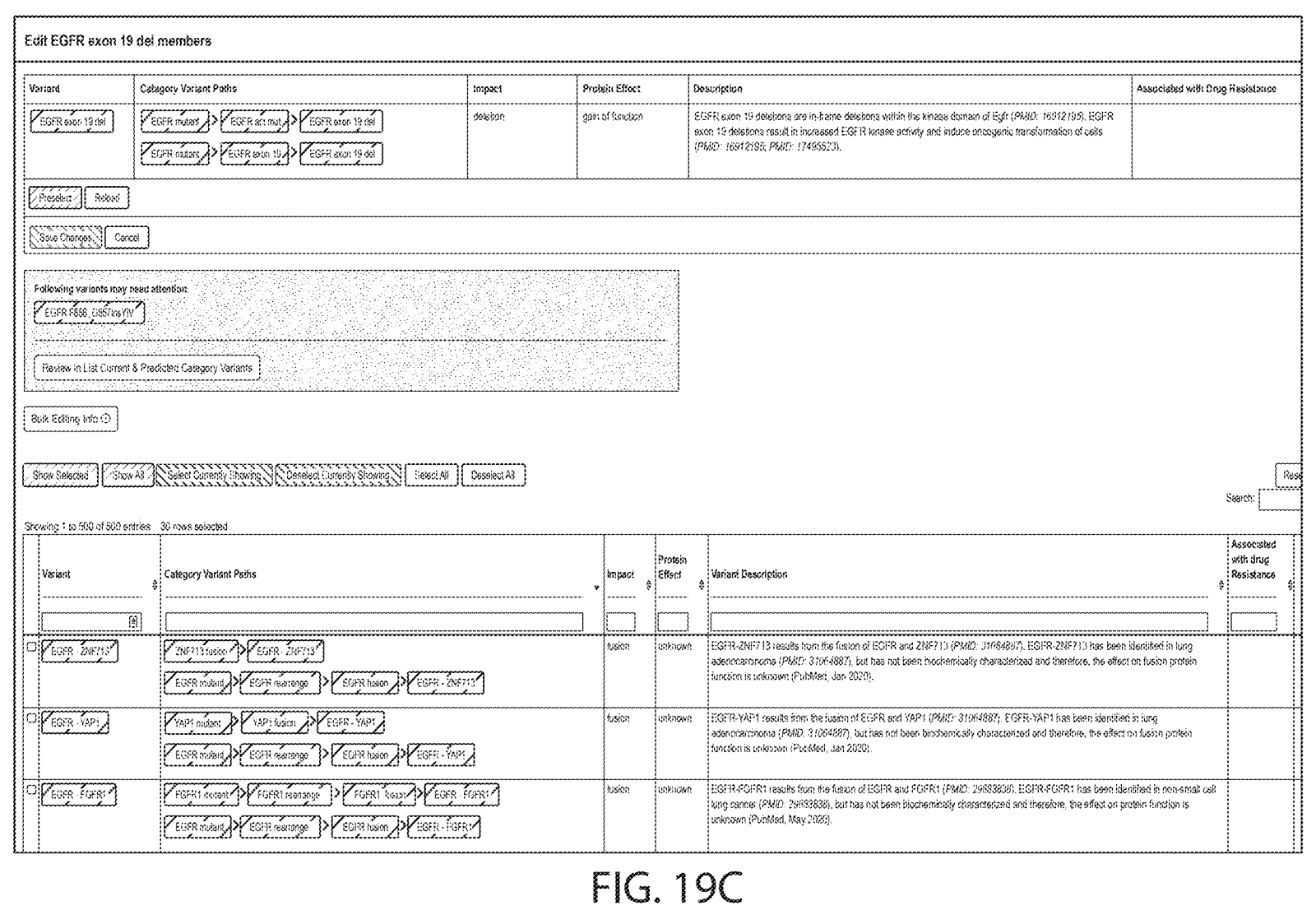

Edit EGFR exon 19 del members

| Variant | Category Variant Paths | Impact | Protein Effect | Description | Associated with Drug Resistance |
|---|---|---|---|---|---|
| EGFR exon 19 del | EGFR mutant > EGFR act mut > EGFR exon 19 del<br>EGFR mutant > EGFR exon 19 > EGFR exon 19 del | deletion | gain of function | EGFR exon 19 deletions are in-frame deletions within the kinase domain of Egfr (*PMID: 16912195*). EGFR exon 19 deletions result in increased EGFR kinase activity and induce oncogenic transformation of cells (*PMID: 16912195; PMID: 17495523*). | |

Predict Reload

Save Changes Cancel

Following variants may need attention:

EGFR F856_G857insYIV

Review in List Current & Predicted Category Variants

Bulk Editing Info

Show Selected Show All Select Currently Showing Deselect Currently Showing Select All Deselect All Res Search:

Showing 1 to 500 of 500 entries 30 rows selected

| | Variant | Category Variant Paths | Impact | Protein Effect | Variant Description | Associated with drug Resistance |
|---|---|---|---|---|---|---|
| ☐ | EGFR - ZNF713 | ZNF713 fusion > EGFR - ZNF713<br>EGFR mutant > EGFR rearrange > EGFR fusion > EGFR - ZNF713 | fusion | unknown | EGFR-ZNF713 results from the fusion of EGFR and ZNF713 (*PMID: 31064887*). EGFR-ZNF713 has been identified in lung adenocarcinoma (*PMID: 31064887*), but has not been biochemically characterized and therefore, the effect on fusion protein function is unknown (PubMed, Jan 2020). | |
| ☐ | EGFR - YAP1 | YAP1 mutant > YAP1 fusion > EGFR - YAP1<br>EGFR mutant > EGFR rearrange > EGFR fusion > EGFR - YAP1 | fusion | unknown | EGFR-YAP1 results from the fusion of EGFR and YAP1 (*PMID: 31064887*). EGFR-YAP1 has been identified in lung adenocarcinoma (*PMID: 31064887*), but has not been biochemically characterized and therefore, the effect on fusion protein function is unknown (PubMed, Jan 2020). | |
| ☐ | EGFR - FGFR1 | FGFR1 mutant > FGFR1 rearrange > FGFR1 fusion > EGFR - FGFR1<br>EGFR mutant > EGFR rearrange > EGFR fusion > EGFR - FGFR1 | fusion | unknown | EGFR-FGFR1 results from the fusion of EGFR and FGFR1 (*PMID: 29883838*). EGFR-FGFR1 has been identified in non-small cell lung cancer (*PMID: 29883838*), but has not been biochemically characterized and therefore, the effect on protein function is unknown (PubMed, May 2020). | |

FIG. 19C

SYSTEMS AND METHODS FOR GENE VARIANT GROUPING AND VISUALIZATION

RELATED APPLICATIONS

This Application is a national stage filing under 35 U.S.C. § 371 of International Patent Application Serial No. PCT/US2021/026625, filed Apr. 9, 2021, entitled "SYSTEMS AND METHODS FOR GENE VARIANT GROUPING AND VISUALIZATION", which claims the benefit under 35 U.S.C. § 119(e) of U.S. Provisional Application Ser. No. 63/008,222, filed Apr. 10, 2020, and entitled "Systems and Methods for Gene Variant Grouping and Visualization." The entire contents of these applications are incorporated herein by reference in their entirety.

BACKGROUND

Next-generation sequencing (NGS)-based sequencing tests can identify a vast number of specific genomic variations in tumor samples. These genetic variations can be associated with different behavior of the cancerous cells within a patient. Such genetic variations can also correlate with the potential response of the cancer to different treatment modalities.

SUMMARY

The present disclosure provides, in some aspects, a clinical treatment decision support tool that builds hierarchical relationships between genetic variants of cancers so that a clinician can more easily assess treatment outcomes associated with a patient's genetic variant. In particular, some embodiments are directed to a method for determining relationships between gene variants of a gene, the gene variants being related to one or more cancers and being correlated to a treatment response of the one or more cancers to one or more treatments. The method comprises: accessing, using at least one processor, a database comprising information about the gene variants, the information including at least information indicative of a treatment response of a first gene variant of the gene variants to one or more treatments; categorizing, using the at least one processor, the information about the gene variants within a plurality of groups; and generating, using the at least one processor, hierarchical relationships between each group of the plurality of groups.

Some embodiments are directed to a system for determining relationships between gene variants of a gene, the gene variants being related to one or more cancers and being correlated to a treatment response of the one or more cancers to one or more medications. The system comprises: at least one processor; and at least one computer memory storing instructions, that, when executed by the at least one processor, perform a method. The method comprises: accessing, using at least one processor, a database comprising information about the gene variants, the information including at least information indicative of a treatment response of a first gene variant of the gene variants to one or more treatments; categorizing, using the at least one processor, the information about the gene variants within a plurality of groups; and generating, using the at least one processor, hierarchical relationships between each group of the plurality of groups.

Some embodiments are directed to at least one non-transitory computer-readable storage medium storing processor-executable instructions that, when executed by at least one processor, cause the at least one processor to perform a method for determining relationships between gene variants of a gene, the gene variants being related to one or more cancers and being correlated to a treatment response of the one or more cancers to one or more medications. The method comprises: accessing a database comprising information about the gene variants, the information including at least information indicative of a treatment response of a first gene variant of the gene variants to one or more treatments; categorizing the information about the gene variants within a plurality of groups; and generating hierarchical relationships between each group of the plurality of groups.

In some embodiments, the method further comprises generating, using the at least one processor, a visualization of the hierarchical relationships between each group of the plurality of groups; and displaying, on a user interface of a computing device, the visualization.

In some embodiments, the act of categorizing further comprises categorizing the information about the gene variants within the plurality of groups such that each member of a group of the plurality of groups is unique.

In some embodiments, categorizing the information about the gene variants further comprises selecting, based on the categorized information about the gene variants within a group of the plurality of groups, an owner member of the group, wherein the owner member comprises information about a group category.

In some embodiments, the act of generating the hierarchical relationships further comprises generating a directed acyclic graph In some embodiments, categorizing the information about the gene variants further comprises: determining, based on information associated with a second gene variant of the gene variants, whether the second gene variant is a specific fusion mutation; conditionally categorizing, based on determining that the second gene variant is a specific fusion mutation, the second gene variant as a member of a fusion group or a rearrange group by determining whether the information associated with the second gene variant includes information indicating that a gene group including the second gene variant includes a fusion group or a rearrange group.

In some embodiments, categorizing the information about the gene variants further comprises: determining, based on information associated with a second gene variant of the gene variants, whether the second gene variant is a fusion mutation; conditionally categorizing, based on determining that the second gene variant is a fusion mutation, the second gene variant as a member of a rearrange group by determining whether the information associated with the second gene variant includes information indicating that a gene group including the second gene variant includes a rearrange group.

In some embodiments, categorizing the information about the gene variants further comprises: determining, based on information associated with a second gene variant of the gene variants, whether the second gene variant is a non-specific mutation type; determining, based on the information associated with the second gene variant, whether the second gene variant is a mutant; determining whether the information associated with the second gene variant includes information indicating that a gene group including the second gene variant includes a mutant group; and conditionally categorizing the second gene variant as a member of a mutant group if: (1) the second gene variant is not a non-specific mutation type, (2) the second gene variant is not a mutant, and (3) the information associated with the second gene variant includes information indicating that a gene group including the second gene variant includes a mutant group.

In some embodiments, categorizing the information about the gene variants further comprises: determining, based on information associated with a second gene variant of the gene variants, whether the second gene variant is a gene variant having an activating protein effect; determining whether the information associated with the second gene variant includes information indicating that a gene group including the second gene variant includes an activating mutation (act mut) group; and conditionally categorizing the second gene variant as a member of an act mut group if: (1) the second gene variant is a gene variant having an activating protein effect and (2) the information associated with the second gene variant includes information indicating that a gene group including the second gene variant includes an act mut group.

In some embodiments, categorizing the information about the gene variants further comprises: determining, based on information associated with a second gene variant of the gene variants, whether the second gene variant is a gene variant having an inactivating protein effect; determining whether the information associated with the second gene variant includes information indicating that a gene group including the second gene variant includes an inactivating mutation (inact mut) group; and conditionally categorizing the second gene variant as a member of an inact mut group if: (1) the second gene variant is a gene variant having an inactivating protein effect and (2) the information associated with the second gene variant includes information indicating that a gene group including the second gene variant includes an inact mut group.

In some embodiments, categorizing the information about the gene variants further comprises: determining, based on information associated with a second gene variant of the gene variants, whether the second gene variant is a positional mutation; determining a codon position of the second gene variant based on the information associated with the second gene variant; comparing the determined codon position of the second gene variant with a codon position of a proposed positional group; and conditionally categorizing the second gene variant as a member of the positional group if the determined codon position of the second gene variant is equal to the codon position of the proposed positional group.

In some embodiments, categorizing the information about the gene variants further comprises: determining whether a second gene variant is a V600E or V600K gene variant based on information associated with the second gene variant; determining whether the information associated with the second gene variant includes information indicating that a gene group including the second gene variant includes a V600E or V600K group; conditionally categorizing the second gene variant as a member of a V600E or V600K group if: (1) the second gene variant is a V600E or V600K gene variant and (2) the information associated with the second gene variant includes information indicating that a gene group including the second gene variant includes a V600E or V600K group.

In some embodiments, categorizing the information about the gene variants further comprises: determining, based on information associated with a second gene variant of the gene variants, whether the second gene variant is a part of a gene-exon map; (1) conditionally determining, based on the determination that the second gene variant is a part of the gene-exon map and the information associated with the second gene variant, if a codon position of the second gene variant is within a positional range of an exon in the gene-exon map; (2) conditionally determining, based on the determination that the second gene variant is a part of the gene-exon map, if the information associated with the second gene variant comprises information indicative of the second gene variant belonging to an exon #indel group; and conditionally categorizing, based on affirmative determinations in (1) and/or (2), the second gene variant as a member of an exon group and/or an exon indel group.

In some embodiments, categorizing the information about the gene variants further comprises: determining, based on information associated with a second gene variant, whether a second gene variant of the gene variants is a frameshift gene variant; determining, based on the information associated with the second gene variant, a codon position of a second gene variant; determining a codon position of a proposed frameshift group; and conditionally categorizing the second gene variant as a member of the proposed frameshift group if the codon position of the second gene variant is equal to the codon position of the frameshift group.

Some embodiments are directed to a method of treating a patient, the patient having a cancer with a gene variant. The method comprises: accessing, using at least one processor, a database comprising information about gene variants associated with cancers, the information including at least information indicative of a treatment response of a first gene variant of the gene variants to one or more treatments; categorizing, using the at least one processor, the information about the gene variants within a plurality of groups; generating, using the at least one processor, hierarchical relationships between each group of the plurality of groups; determining, using the hierarchical relationships between each group and the information indicative of a treatment response of a first gene variant, a treatment modality correlated with the gene variant; and treating the patient using the treatment modality.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

FIG. 16 illustrates an example of a user interface displaying information related to the KRAS gene variant, KRAS G12E, genetic mutations thereof, and their relation to cancer therapies, in accordance with some embodiments described herein.

FIG. 17 illustrates an example of a user interface configured to allow a user to review gene variants whose stored category memberships do match those predicted by the variant category engine, in accordance with some embodiments described herein.

FIG. 18 illustrates an example of a user interface displaying gene variant categories related to the KRAS gene, in accordance with some embodiments described herein.

FIG. 19B illustrates an example of a user interface configured to display differences between a user's selection of categories associated with a gene variant and predicted categories, in accordance with some embodiments described herein.

FIG. 19C illustrates an example of a user interface configured to enable a user to edit information associated with a category variant, in accordance with some embodiments described herein.

DETAILED DESCRIPTION

Figure 1A:
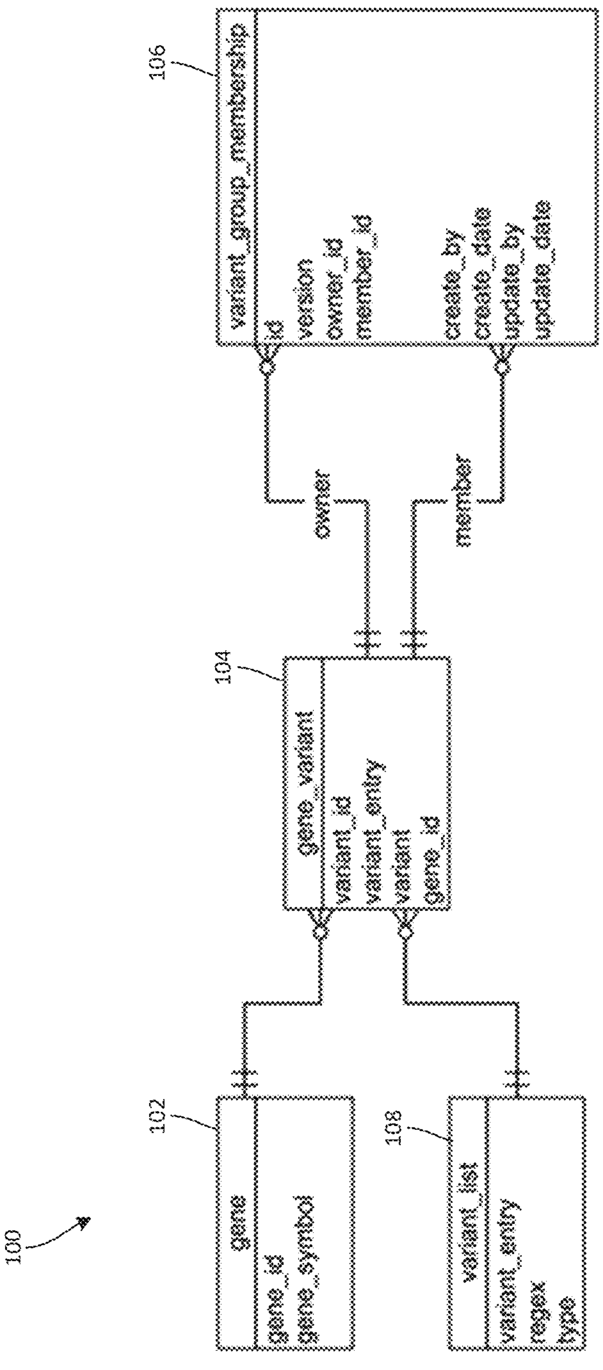
FIG. 1A illustrates an example of an entity relationship diagram for recording gene variant groups, in accordance with some embodiments described herein.

Identifying genetic mutations associated with a patient's cancer can inform clinicians and/or researchers about the effectiveness of different treatment options for the patient's particular cancer. For example, enasidenib is FDA-approved for treatment in IDH2 R172 W mutant acute myeloid leukemia, dabrafenib is FDA-approved for treatment of BRAF V600E mutant melanoma, and larotrectinib is FDA-approved for treatment of any solid tumor with an NTRK fusion. However, the current labeling practices for FDA-approved cancer treatments, professional guidelines, and clinical trial recruitment criteria can make it difficult for a clinician or researcher to determine the particular usefulness of a treatment. Treatments such as medications and/or clinical trial recruitment guidelines are often labeled very generically. For example, treatments may be labeled with generic mutation terms or categories such as "EGFR activating mutations," "NTRK fusions," or "PDGFRA exon 18 mutations." Determining which specific genetic mutations may be responsive to such generically-labeled treatments presents a challenge to medical practitioners, and tying a patient's specific genetic variations to these treatments can be a major hurdle for medical practitioners in deciding on a treatment option for a patient, particularly given the large number of genetic mutations associated with cancers and the number of available treatment options.

The inventors have recognized that organizing and visualizing this information quickly and in a manner that is easy to understand and navigate can enable clinicians to appropriately prescribe an effective treatment (e.g., a particular medication, a clinical trial) to their patients. Accordingly, they have developed systems and methods for determining relationships between gene variants of a gene and correlated responses to cancer treatments. Additionally, the inventors have developed systems and methods for visualizing the relationships between gene variants of a gene. By visualizing these relationships (e.g., in a sunburst plot), a clinician may be able to start with a act mutation of interest and holistically navigate through broader categorizations and relationships with treatment options to determine potential treatment options for their patient.

The inventors have further recognized and appreciated that organizing a large volume of information about genes and gene variants can be done quickly and effectively by implementing hierarchical relationships between gene variants (e.g., as a directed acyclic graph (DAG)). For example, there are over 1700 genes currently associated with cancers. Each of these genes can have up to, or even more than, 500 variants (e.g., different mutation types) that may affect treatment outcomes for a patient. The inventors have recognized that implementing hierarchical relationships between these gene variants can prevent recursion and increase the speed of re-organizing the data in response to updates based on new research findings and/or to dynamically visualize the information and relationships.

As cancer genomic research continues to evolve, new gene variants and/or new categories may be added to the graph, necessitating the rebuilding of the full graph and/or portions of the graph. Implementing hierarchical relationships in the form of a DAG has, for example, reduced the time to build the full graph describing these relationships to between 20 and 30 seconds, down from several minutes per gene. Accordingly, the implementation of hierarchical relationships has reduced the time to build the full graph such that the graph may be dynamically and quickly updated as needed (e.g., based on new research findings). The reduced speed of building the full graph achieved by implementing hierarchical relationships can thus enable faster, more efficient, and more timely updating of the graph with results from cutting-edge research.

In some embodiments, a method for determining relationships between gene variants of a gene may be provided. The gene variants may be related to one or more cancers and may be correlated to a treatment response of the one or more cancers to one or more medications. The method may include accessing, using at least one processor, a database (e.g., stored in local computer memory or remotely, e.g., via a cloud computing system) comprising information about the gene variants, the information including at least information indicative of a treatment response of each gene variant of the gene variants to one or more medications. For example, the information may include FDA guidelines, results from Phase I trials, and/or results from clinical studies. The method may include categorizing, using the at least one processor, the information about the gene variants within a plurality of groups, and generating, using the at least one processor, hierarchical relationships between each group of the plurality of groups.

In some embodiments, the method may also include treating a patient, the patient having a cancer with a gene variant. In such embodiments, the method may further include determining a treatment modality for the cancer with a gene variant. Determining the treatment modality may be performed using the generated hierarchical relationships between each group and the information indicative of a treatment response of the gene variant. For example, a medical practitioner may determine based on the hierarchical relationships that the patient's cancer has a gene variant that, though the patient's gene variant has not been clinically recorded as having a particular response to a treatment (e.g., an FDA-approved medication, a treatment associated with Phase I results, and/or a clinical trial in recruitment), is a member of a larger category of variants that are correlated with successful treatment responses from said treatment. The method may further include treating the patient using the determined treatment (e.g., by administering the selected medication).

In some embodiments, the information may be categorized into a plurality of groups according to a set of rules configured to enforce hierarchical relationships between groups (e.g., to enforce a directed acyclic graph (DAG)). Such hierarchical relationships may enforce that a group may not contain an ancestor as a group entry. FIG. 1A illustrates an example of an Entity Relationship Diagram 100 (e.g., a data structure) configured to store gene variant groups and to enforce such hierarchical relationships, according to some embodiments. In the example of FIG. 1A, a gene group 102 is associated with information identifying the gene group (e.g., gene names, identification numbers, etc.) and comprises groups of gene variants 104.

In some embodiments, a group of gene variants 104, or category variant, is associated with information identifying the gene variants (e.g., variant names, identification numbers, gene names, etc.). The members of the group of gene variants 104 are shown in the variant group membership 106. The variant group members 106 include an owner, which identifies the group of gene variants 104, and one or more member gene variants ("member"). Both the owner and member gene variants may be associated with identifying information (e.g., names, identification numbers, etc.) and chronological information (e.g., creation date, update date, etc.).

In some embodiments, members of each group (e.g., groups of gene variant groups that are members of a gene group, or groups of gene variants that are members of a gene variant group) are unique such that no repetitions occur within a group. Additionally, in some embodiments, a child member (e.g., a gene variant) cannot be a member of both a parent group (e.g., a category) and the parent group's parent, thereby defining the graph as a DAG. For example, a specific gene variant cannot be a member of both the exon 2 category variant and a member of the exon 2 category variant's parent category, the positional category. Alternatively or additionally, in some embodiments, the DAG may be defined by the rule that a parent group cannot be a member of a child group.

In some embodiments, there may be several gene variant types 108 to represent the many ways genetic mutations may manifest. Examples of such gene variants are shown in Table 1 herein. In some embodiments, and as shown in the example of Table 1, each variant entry may be accompanied by a regular expression ("regex") to specify the format of the variant name as shown by the group visualization process. Each category type may be associated with additional categorization rules, as described herein.

In some embodiments, the gene variant types may include a category type of "(X)aa #X," which may indicate that a variant exists on a gene such that an amino acid at a specific position within the gene has been substituted with another amino acid. As an example, the BRAF gene, which can be related to colorectal cancers, exhibits several such gene variants, including the V600E and V600K gene variants.

In some embodiments, the gene variant types may include a category type of "act mut," which may indicate that the gene variant results in a gain of function with respect to protein effect. For example, the gene variant AKT1 E17K has a protein effect that confers a gain of function to the gene AKT1, as compared to the wild-type AKT1 protein.

In some embodiments, the gene variant types may include a category type of "inact mut," which may indicate that the variant results in a loss of function with respect to protein effect. For example, APC N1026S has a protein effect that confers a loss of function to the gene APC, as compared to the wild-type APC protein.

TABLE 1

| variant_entry | regex | Definition | Type |
|---|---|---|---|
| (X)aa#X | [ACDEFGHIKLMNPQRSTVWY][0-9] + X | Indicates that the variant results in the replacement of the amino acid at the specified position by another amino acid. The variant can be considered a category containing any variant resulting in an amino acid substitution at the specified position. An example would be 'BRAF V600X'. | Category |

TABLE 1-continued

| variant_entry | regex | Definition | Type |
|---|---|---|---|
| act mut | act mut | Indicates that the variant results in a gain of protein function. This can be considered a category containing any variant that results in a gain of function. In some cases, such as with small GTPases, this may indicate that the variant results in a loss of intrinsic function, resulting in activation of downstream signaling. In these cases, this can be considered a category that contains loss of function and/or gain of function variants resulting in downstream pathway activation. | Category |
| class # | class [1-3] | Indicates a category of variants with a similar mechanism for activation or inactivation of downstream signaling. This can also indicate a variant belonging to that category. | Category |
| exon # indel | exon [0-9] + (ins\|del) | Indicates an insertion (ins) or deletion (del) in the specified exon of the gene. This can be considered a category containing any variant resulting from an insertion or deletion in the specified exon. An example would be 'FLT3 exon 14 ins'. | Category |
| exonX | exon[0-9]+ | Indicates a mutation in the specified exon. This can be considered a category containing any variant within the specified exon. | Category |
| fusion | fusion | Indicates a fusion of the gene, but the fusion partner is unspecified. This can be considered a category containing any fusion in which the specified gene is a partner. | Category |
| inact mut | inact mut | Indicates that the variant results in a loss of protein function. This can be considered a category containing any variant that results in a loss of function. | Category |
| mutant | mutant | Indicates an unspecified mutation in the gene. This can be considered a category containing any missense, indel, nonsense, or frameshift variant in the gene. | Category |
| rearrange | rearrange | Indicates an unspecified rearrangement of the gene. This can be considered a category containing rearrangement of the specified gene. | Category |
| V600E/K | V600E/K | A category variant for BRAF V600E and V600K | Category |
| Xaa#fs | [ACDEFGHIKLMNP QRSTVWY][0-9] + fs | Indicates a frameshift at the specified amino acid. This can be considered a category containing any long format frameshift variants occurring at the same amino acid. | Category |

In some embodiments, the gene variant types may include a category type of "exon #indel," which may indicate that an insertion or deletion has occurred at a nonspecified location in an exon. For example, the gene EGFR may include a deletion at exon 19 ("exon 19 del") or an insertion at exon 20 ("exon 20 ins").

In some embodiments, the gene variant types may include a category type of "Xaa #X," or a positional variant, which may indicate a mutation at a specified codon. For example, the KRAS gene may include a missense mutation at codon position 12 ("KRAS G12X").

In some embodiments, the gene variant types may include a category type of "fusion," which may indicate a fusion of the gene. A fusion gene may be a hybrid gene formed from two previously independent genes and may result from a translocation, interstitial deletion, chromosomal inversion, or other such genetic mutations. Members of the fusion category may be a gene variant with a specific genetic fusion or may be a gene that is a fusion partner gene.

In some embodiments, the gene variant types may include a category type of "mutant," which may indicate an unspecified mutation in the gene. An unspecified mutation may be any variant on a gene that is not the mutant category variant itself and is not a variant with a type of "non-specific." The mutant category type may include gene variants that are categorized into any of the other categories described herein, but may not include gene variants that are categorized into category variants that are themselves members of the mutant category.

In some embodiments, the gene variant types may include a category type of "rearrange," which may indicate an unspecified rearrangement of the gene. A gene variant may be categorized as a rearrange gene variant if the gene variant is a fusion partner gene or is otherwise involved in a gene fusion.

In some embodiments, the gene variant types include a category type of "Xaa #fs," or a frameshift category type, which may indicate a frameshift mutation of the gene. A gene variant may be categorized as a frameshift gene variant if the gene variant contains any frameshift mutation at a specified amino acid location in the gene.

Following below are more detailed descriptions of various concepts related to, and embodiments of cancer-related gene variant categorization techniques. It should be appreciated that various aspects described herein may be implemented in any of numerous ways. Examples of specific implementations are provided herein for illustrative purposes only. In addition, the various aspects described in the embodiments below may be used alone or in any combinations and are not limited to the combinations explicitly described herein.

Figure 1B:
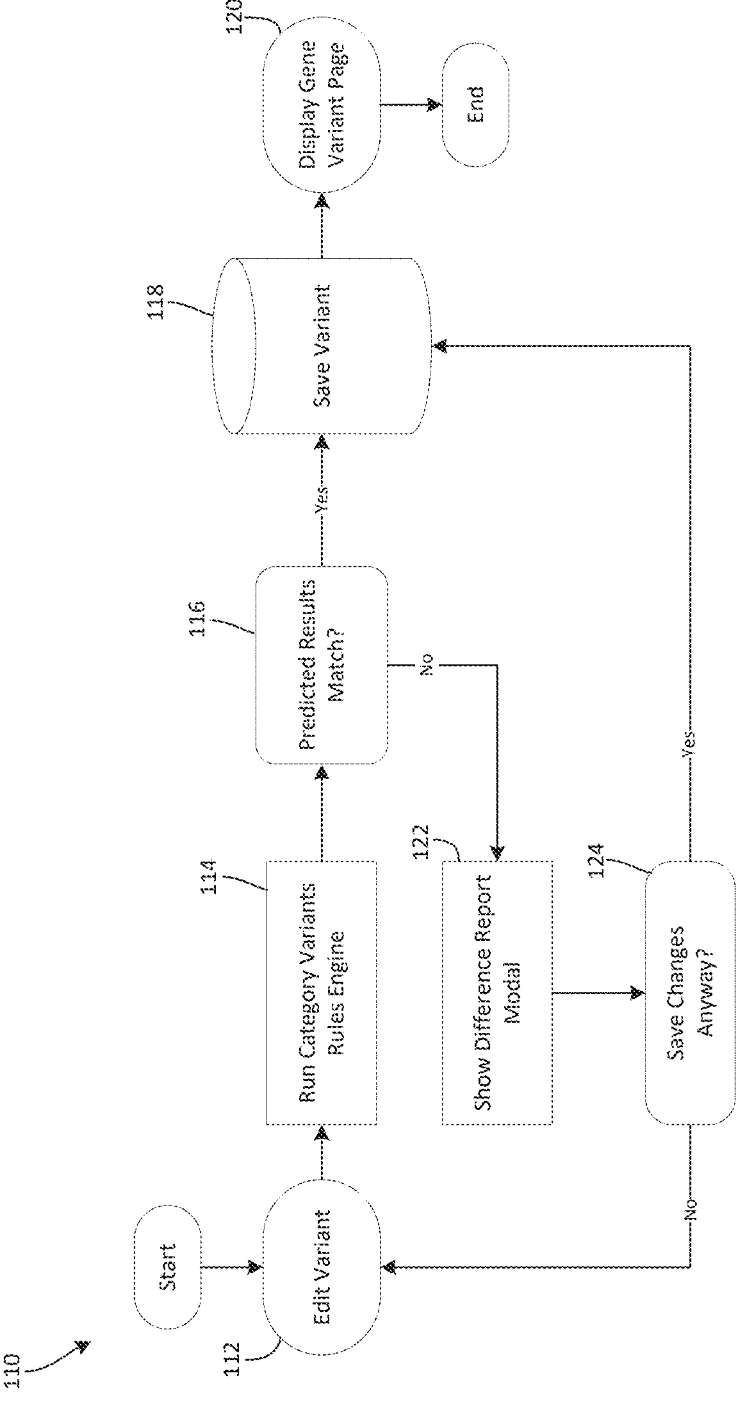
FIG. 1B illustrates a block diagram of a process to edit a category variant association using a variant category engine, in accordance with some embodiments described herein.
Figure 20:
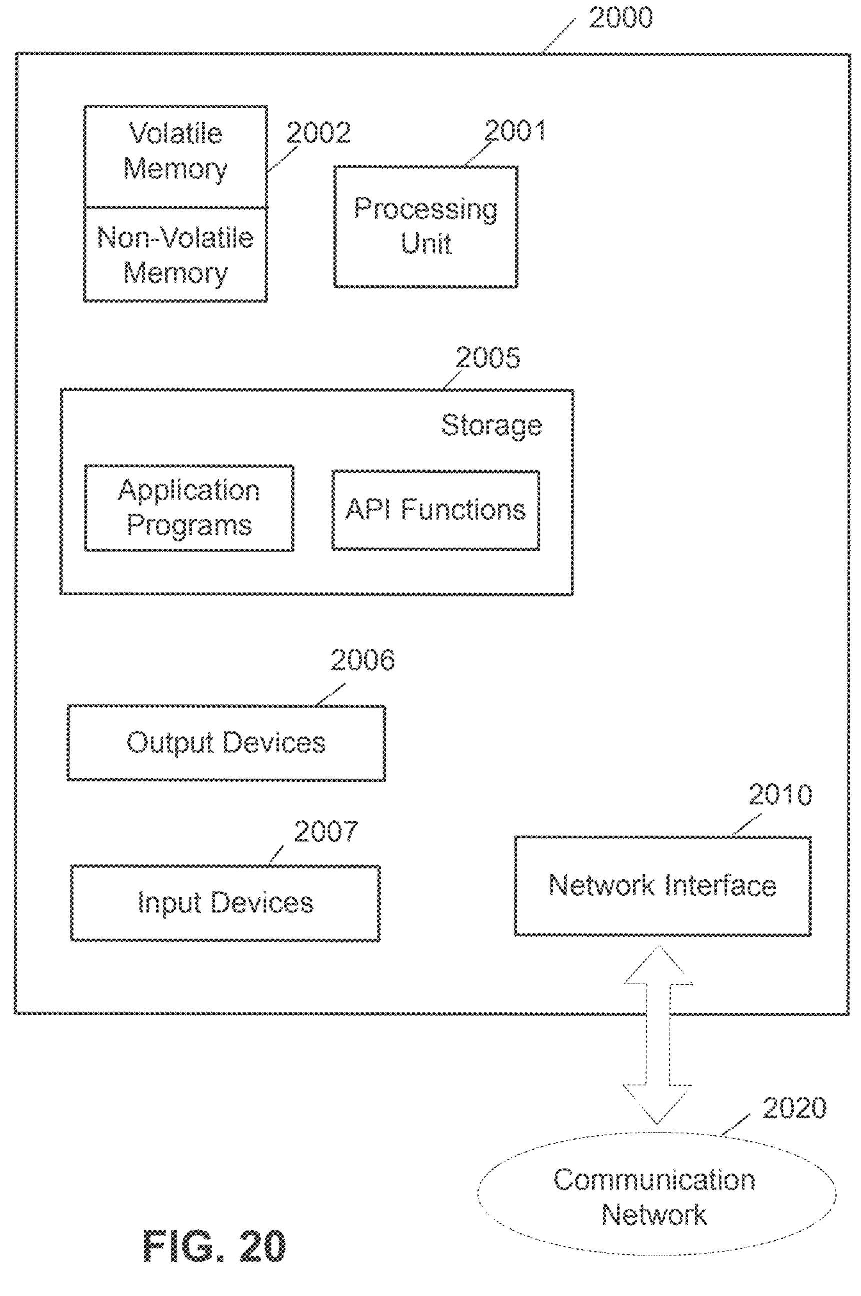
FIG. 20 depicts, schematically, an illustrative computing device 2000 on which any aspect of the present disclosure may be implemented.

FIG. 1B illustrates a block diagram of a process 110 performed by a variant category engine (e.g., as implemented by a computing device such as the computing device of FIG. 20) to edit a category variant association, in accordance with some embodiments described herein. A system operator (e.g., a user) may, in some embodiments, choose to manually edit a gene variant in the network (e.g., to input new information such as information from clinical trial results) at act 112. After the system operator edits a gene variant, a variant category engine performs a process at act 114, described in more detail in connection with FIG. 2, to compare the category variants selected by the system operator with any predicted category variants in order to update the gene variant relationships stored in the data structure of FIG. 1A.

In some embodiments, the process may compare results of the comparison with predicted results at act 116. If the results do not match, the system may show a report to the system operator at act 124 if any differences between the selected category variants and predicted category variants are found. The system operator may choose to save the edits at act 118 even if differences were detected at act 116, or the system operator may choose to further edit the gene variant by returning to act 112. If the comparison at act 116 yielded no differences, then the system may proceed to act 118 and automatically save any updates made to the data structure. Thereafter, the updated categories associated with the gene variant may be displayed at act 120 (e.g., by being displayed on a screen associated with a computing device, by being transmitted to another device, or by otherwise being communicated in any suitable manner to the system operator).

Figure 2:
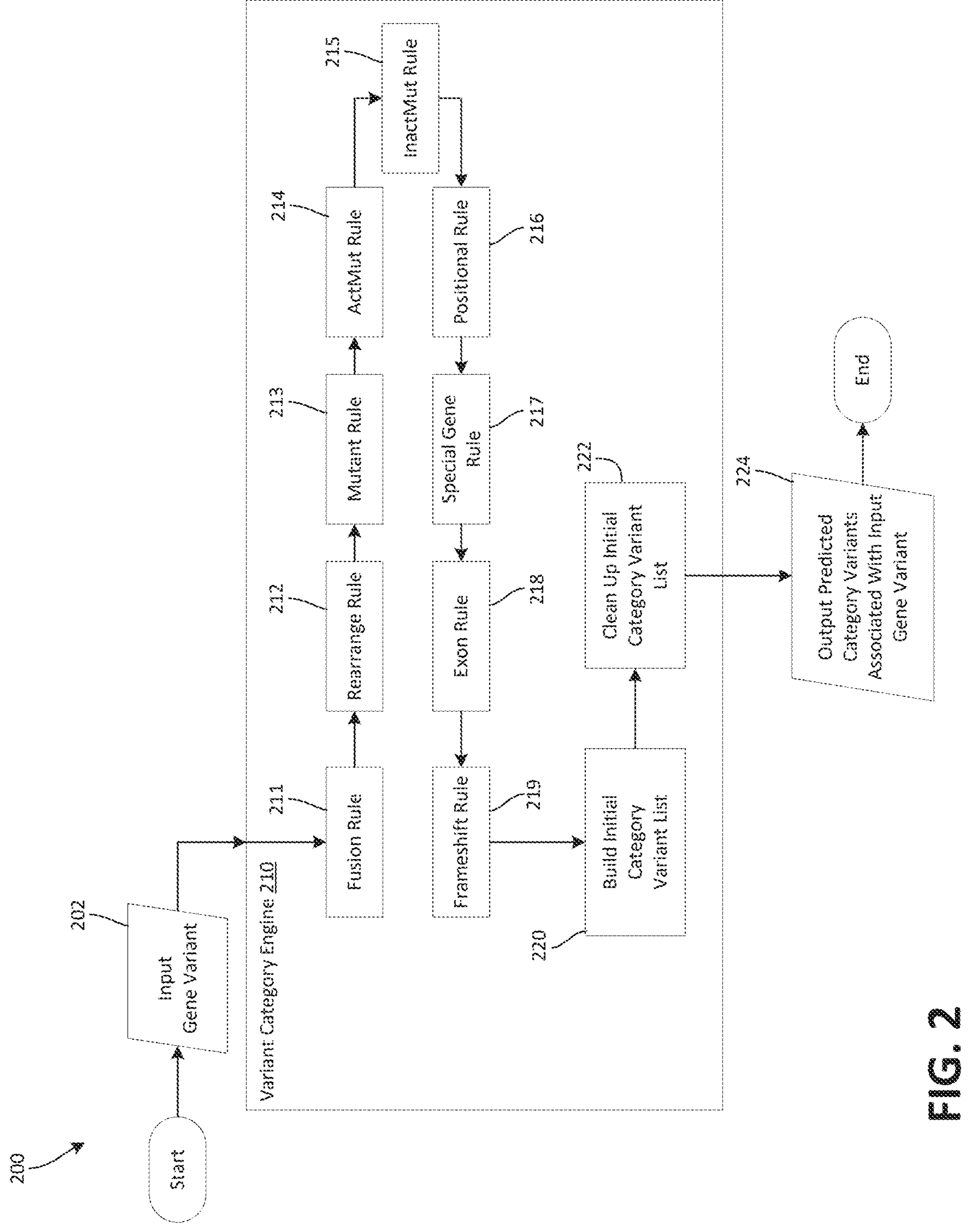
FIG. 2 illustrates a block diagram of a process performed by a variant category engine to apply a series of rules and propose a list of category variants that a gene variant could be a member of, in accordance with some embodiments described herein.

FIG. 2 illustrates a block diagram of a process 200 performed by a variant category engine 210 (e.g., as implemented by a computing device such as the computing device 2000 of FIG. 20, or any other suitable computing device) to apply a series of rules and propose a list of category variants that a gene variant could be a member of, in accordance with some embodiments described herein. The variant category engine 210 may be used in conjunction with the process of FIG. 1B, in some embodiments, and may impose a hierarchy on the gene variants and category variants as described in connection with the data structure 100 of FIG. 1A.

In some embodiments, a gene variant 202 is input (e.g., by a system operator) to the variant category engine 210 for categorization. The gene variant 202 is associated with information such as the gene name, category variants associated with the gene, the location of the gene variant 202, and/or the codon position of the gene variant 202. The variant category engine 210 may then apply a series of rules in order to generate a list of category variants that the input gene variant may be a member of. The rules may include a Fusion Rule 211, a Rearrange Rule 212, a Mutant Rule 213, an ActMut Rule 214, an InactMut Rule 215, a Positional Rule 216, a Special Gene Rule 217, an Exon Rule 218, and/or a Frameshift Rule 219. These rules are described in more detail in connection with FIGS. 4 through 12. It should be appreciated that variant category engine 210 may include fewer than or all of these rules, may include additional rules, or may have these rules disposed in a different order than shown in the example of FIG. 2, in some embodiments. In some embodiments, the rules may be performed in parallel (e.g., using a distributed computing system).

In some embodiments, after applying the rules 211 through 219 to the gene variant 202 the variant category engine 210 may build an initial category variant list at act 220. Thereafter, the variant category engine 210 may clean up the initial category variant list at act 222. The variant category engine 210, at act 222, may analyze the hierarchical relationships present between members of the initial category variants list and eliminate any category variants that violate the hierarchical rules of the DAG. For example, the variant category engine 210 may eliminate any category variants that are duplications or may eliminate any relationships that are recursive. In this manner, the variant category engine 210 may impose the hierarchy of a directed acyclic graph on the category variant list output at act 220. Thereafter, at act 224, the process 200 may output the predicted category variants associated with the gene variant 202. The list of category variants may be output by any suitable means, including by displaying to a user, by saving to a computer memory, and/or by transmitting to another computing device. Alternatively, the list of category variants may be maintained in computer memory for further processing (e.g., as described in connection with act 116 of FIG. 1B).

Figure 3:
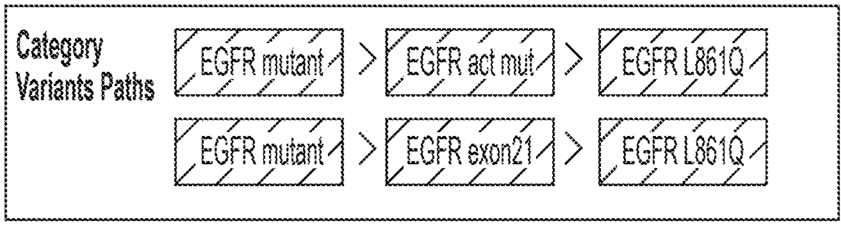
FIG. 3 illustrates an example gene variant categorization resulting from the processes of FIGS. 1A and 2, in accordance with some embodiments described herein.

FIG. 3 illustrates an example of an output from the processes of FIGS. 1A and 2, in accordance with some embodiments described herein. As an example, given the input gene variant EGFR L861Q, if the variant category engine generates a list of candidate category variants including the categories "EGFR mutant," "EGRF act mut," and "EGFR exon 21," the result clean up module may remove "EGFR mutant" from the list of candidate category variants that EGRF L861Q may be a member of because "EGFR mutant" is an ancestor of "EGRF act mut" and "EGFR exon 21." The end result may be the proposal that EGRF L861Q should be a member of both "EGFR act mut" and "EGFR exon 21," and would be associated with "EGFR mutant" as both "EGFR act mut" and "EGFR exon21" are members of "EGFR mutant."

Figure 4:
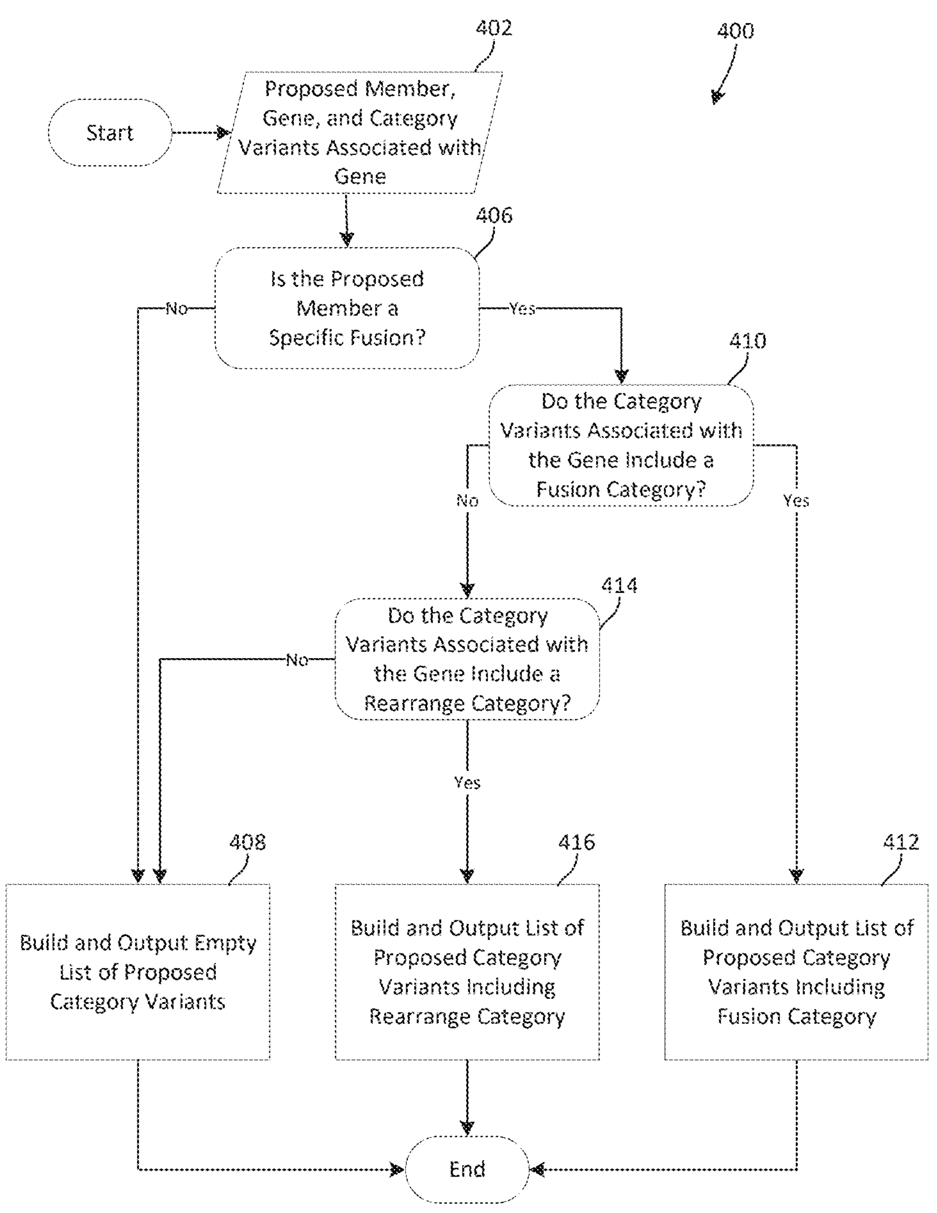
FIG. 4 illustrates a block diagram of a process for applying a fusion rule, in accordance with some embodiments described herein.

FIG. 4 illustrates a block diagram of a process 400 for applying a Fusion Rule, in accordance with some embodiments described herein. In some embodiments, the Fusion Rule may be applied to a gene variant by the variant category engine of FIG. 2 (e.g., as Fusion Rule 211) or may be implemented independently by any suitable computing device (e.g., the computing device 2000 as described in connection with FIG. 20). In some embodiments, the computing device may pass information 402 to the Fusion Rule including the proposed member (e.g., a gene variant, a category variant, or any other suitable group) and all information associated with the proposed (e.g., location, protein effects, associated treatments), the gene group associated with the proposed member, and a list of category variants associated with the gene group.

In some embodiments, the computing device may then proceed to act 406, where the computing device determines whether the proposed member is a specific fusion mutation. For example, the computing device may determine if the information associated with the proposed member (e.g., stored in the data structure 100) includes information specifying that the member is a specific fusion.

In some embodiments, if the proposed member is a specific fusion, the computing device may then proceed to act 410 to determine if any of the category variants associated with the gene group are an instance of a fusion category variant. For example, the computing device may compare information stored in the list of category variants provided in information 402 and determine if the stored information indicates any members of the list are a fusion category. If the category variants associated with the gene include a fusion category, then the computing device may proceed to act 412 where it builds and outputs a list including the fusion category variants as determined at act 410.

In some embodiments, if, at act 410, no fusion category variant is located within the list of category variants associated with the gene, the computing device will proceed to act 414. At act 414, the computing device may determine if the list of category variants associated with the gene include any rearrange category variants. If the computing device finds one or more rearrange category variants in the list of category variants associated with the gene, then the computing device may proceed to act 416 where the computing device may build and output a list of category variants including the rearrange category variants.

In some embodiments, if the computing device determines that the proposed member is not a specific fusion at act 406 or that the category variants do not include a rearrange category variant at act 414, the computing device may proceed to act 408. At act 408, the computing device may build and output an empty list, as the proposed member has been determined to be associated with neither a fusion nor a rearrange category variant.

In some embodiments, after the computing device has built a list of proposed category variants in acts 412 and 416, or after the computing device has built an empty list in act 408, the computing device may output the generated list. The computing device may output the list by communicating it to a system operator in any suitable manner (e.g., displaying on a screen, transmitting to another computing device, etc.). Alternatively or additionally, the computing device may store the list in computer memory for later use (e.g., for later use by the variant category engine 210 to build the initial category variant list). Alternatively or additionally, the computing device may output the list by passing the list to another rule within the variant category engine 210.

Figure 5:
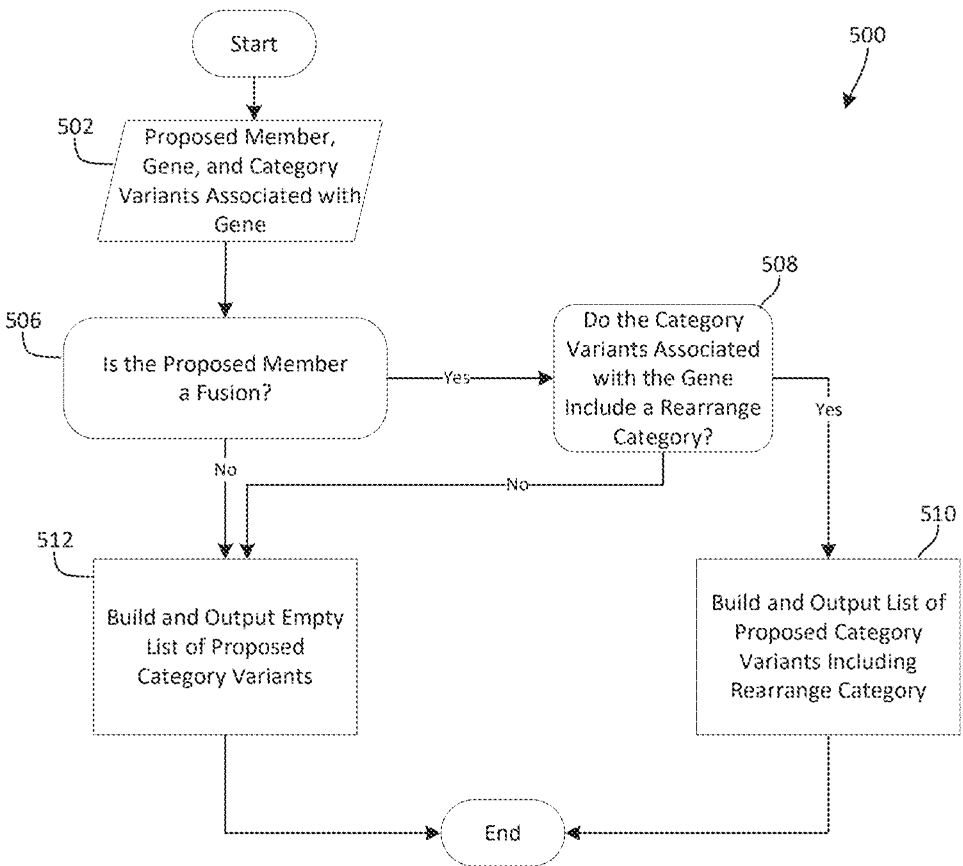
FIG. 5 illustrates a block diagram of a process for applying a rearrange rule, in accordance with some embodiments described herein.

FIG. 5 illustrates a block diagram of a process 500 for applying a Rearrange Rule, in accordance with some embodiments described herein. In some embodiments, the Rearrange Rule may be applied to a gene variant by the variant category engine 210 of FIG. 2 (e.g., as Rearrange Rule 212) or may be implemented independently by any suitable computing device (e.g., the computing device 2000 as described in connection with FIG. 20). In some embodiments, the computing device may pass information 502 to the Rearrange Rule including the proposed member (e.g., a gene variant, a category variant, or any other suitable group) and all information associated with the proposed (e.g., location, protein effects, associated treatments), the gene group associated with the proposed member, and a list of category variants associated with the gene group.

In some embodiments, the computing device may begin at act 506 by determining if the proposed member is a fusion mutation. For example, the computing device may determine whether the proposed member is already a member of a fusion category variant group. In some embodiments, if the computing device determines that the proposed member is a fusion mutation, the computing device may proceed to act 508 where the computing device may determine whether the category variants associated with the gene include a rearrange category.

In some embodiments, if the computing device determines that the category variants associated with the gene include a rearrange category, the computing device may proceed to act 510 where it builds and outputs a list of proposed category variants to be associated with the proposed member, the list including the one or more rearrange categories found in act 508. In some embodiments, if the computing device determines that the proposed member is not a fusion at act 506 or that the list of category variants associated with the gene do not include a rearrange category at act 508, then the computing device may build and output an empty list at act 512.

In some embodiments, after the computing device has built a list of proposed category variants in act 510 or after the computing device has built an empty list in act 512, the computing device may output the generated list. The computing device may output the list by communicating it to a system operator in any suitable manner (e.g., displaying on a screen, transmitting to another computing device, etc.). Alternatively or additionally, the computing device may store the list in computer memory for later use (e.g., for later use by the variant category engine 210 to build the initial category variant list). Alternatively or additionally, the computing device may output the list by passing the list to another rule within the variant category engine 210.

Figure 6:
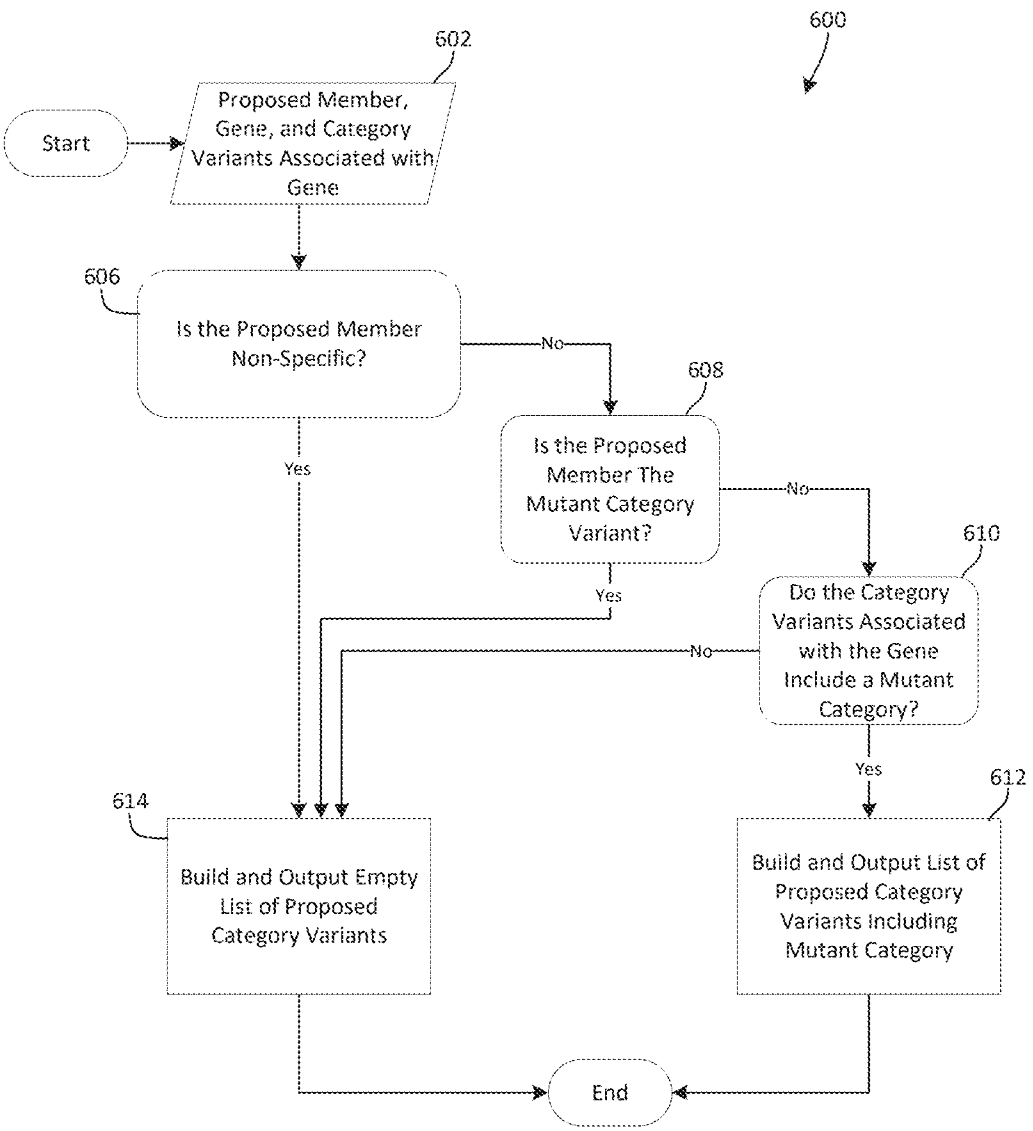
FIG. 6 illustrates a block diagram of a process for applying a mutant rule, in accordance with some embodiments described herein.

FIG. 6 illustrates a block diagram of a process 600 for applying a Mutant Rule, in accordance with some embodiments described herein. In some embodiments, the Mutant Rule may be applied to a gene variant by the variant category engine 210 of FIG. 2 (e.g., as Mutant Rule 213) or may be implemented independently by any suitable computing device (e.g., the computing device 2000 as described in connection with FIG. 20). In some embodiments, the computing device may pass information 602 to the Mutant Rule including the proposed member (e.g., a gene variant, a category variant, or any other suitable group) and all information associated with the proposed (e.g., location, protein effects, associated treatments), the gene group associated with the proposed member, and a list of category variants associated with the gene group.

In some embodiments, computing device may begin at act 606 by determining if the proposed member is a non-specific variant type. A non-specific variant type may represent a genetic variant that is different than a typical genetic mutation, such as, for example, copy number variations and/or information relating to wild-type genes. In some embodiments, the computing device may determine whether the proposed member is a non-specific variant type by determining whether the information associated with the proposed member indicates that the proposed member is a non-specific variant type (e.g., if the "Type" information as shown in Table 1 indicates "Non-Specific"). If the computing device determines that the proposed member is a non-specific variant type at act 606, the computing device may proceed to act 614 where it may build and output an empty list of proposed category variants.

In some embodiments, if the computing device determines at act 606 that the proposed member is not a non-specific variant type, the computing device may proceed to act 608 where the computing device may determine if the proposed member is the mutant category variant. For example, the computing device may determine whether the information associated with the proposed member includes an indication that the proposed member is the mutant category variant (e.g., the proposed member is the owner of the mutant category variant group). In some embodiments, if the computing device does determine, at act 608, that the proposed member is the mutant category variant, the computing device may proceed to act 614 where it may build and output an empty list of proposed category variants.

In some embodiments, if the computing device determines at act 608 that the proposed member is not the mutant category variant, the computing device may proceed to act 610 where the computing device may determine whether the list of category variants associated with the gene provided at act 602 include a mutant category. For example, the computing device may determine whether the information associated with each category variant in the list of category variants indicates that one or more categories are a mutant category variant (e.g., by determining whether the regex is "mutant"). In some embodiments, if the computing device determines that the list of category variants associated with the gene does not include a mutant category, then the computing device may proceed to act 614 where it may build and output an empty list of proposed category variants.

In some embodiments, if the computing determines at act 610 that the list of category variants associated with the gene include a mutant category, then the computing device may proceed to act 612 where it may build and output a list including the one or more determined mutant categories from the list of category variants associated with the gene provided at act 602. In some embodiments, after the computing device has built a list of proposed category variants in act 612 or after the computing device has built an empty list in act 614, the computing device may output the generated list. The computing device may output the list by communicating it to a system operator in any suitable manner (e.g., displaying on a screen, transmitting to another computing device, etc.). Alternatively or additionally, the computing device may store the list in computer memory for later use (e.g., for later use by the variant category engine 210 to build the initial category variant list). Alternatively or additionally, the computing device may output the list by passing the list to another rule within the variant category engine 210.

Figure 7:
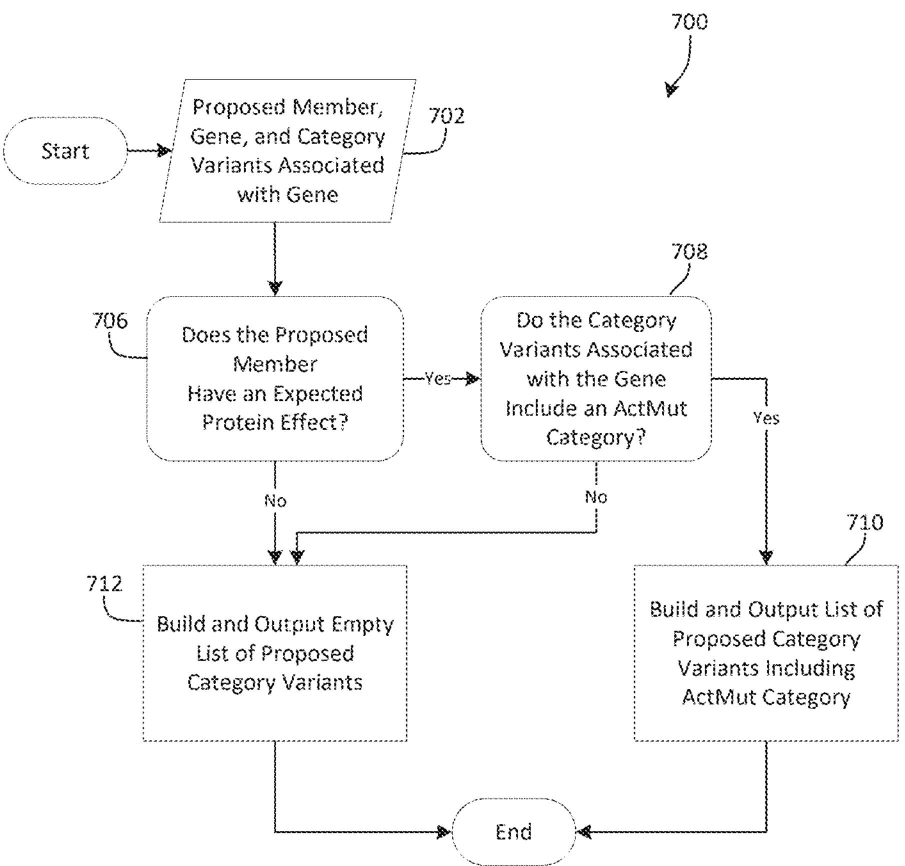
FIG. 7 illustrates a block diagram of a process for applying an ActMut rule, in accordance with some embodiments described herein.

FIG. 7 illustrates a block diagram of a process 700 for applying an ActMut Rule, in accordance with some embodiments described herein. In some embodiments, the ActMut Rule may be applied to a gene variant by the variant category engine of FIG. 2 (e.g., as ActMut Rule 214) or may be implemented independently by any suitable computing device (e.g., the computing device 2000 as described in connection with FIG. 20). In some embodiments, the computing device may pass information 702 to the ActMut Rule including the proposed member (e.g., a gene variant, a category variant, or any other suitable group) and all information associated with the proposed (e.g., location, protein effects, associated treatments), the gene group associated with the proposed member, and a list of category variants associated with the gene group.

In some embodiments, the computing device may begin at act 706 where the computing device may determine whether the proposed member has an expected protein effect that is considered activating (e.g., causing a "gain of function"). For example, the computing device may evaluate the information associated with the proposed member and determine whether the information includes information indicative of an activating protein effect. Alternatively or additionally, the computing device may compare the information associated with the proposed member with a list of known activating protein effects and determine whether the information includes one or more of the known activating protein effects.

If the computing device determines that the proposed member is associated with information indicative of an activating protein effect at act 706, then the computing device may proceed 708, in some embodiments. At act 708, the computing device may determine whether the list of category variants associated with the gene provided at 702 include an act mut ("activating mutation") category. In some embodiments, the computing device may also determine, at act 708, whether the proposed member is the act mut category variant (e.g., if the proposed member is the owner of the act mut category variant group). If the computing device determines that the list of category variants includes an act mut category and/or that the proposed member is not the act mut category variant, then the computing device may proceed to act 710 and build and output a list of proposed category variants including the one or more act mut categories found in the list of category variants associated with the gene.

In some embodiments, if the computing devices determines that the proposed member does not have an activating protein effect at act 706 or does not find an associated act mut category at act 708, then the computing device will proceed to act 712. At act 712, the computing device may build and output an empty list.

In some embodiments, after the computing device has built a list of proposed category variants in act 710 or after the computing device has built an empty list in act 712, the computing device may output the generated list. The computing device may output the list by communicating it to a system operator in any suitable manner (e.g., displaying on a screen, transmitting to another computing device, etc.). Alternatively or additionally, the computing device may store the list in computer memory for later use (e.g., for later use by the variant category engine 210 to build the initial category variant list). Alternatively or additionally, the computing device may output the list by passing the list to another rule within the variant category engine 210.

Figure 8:
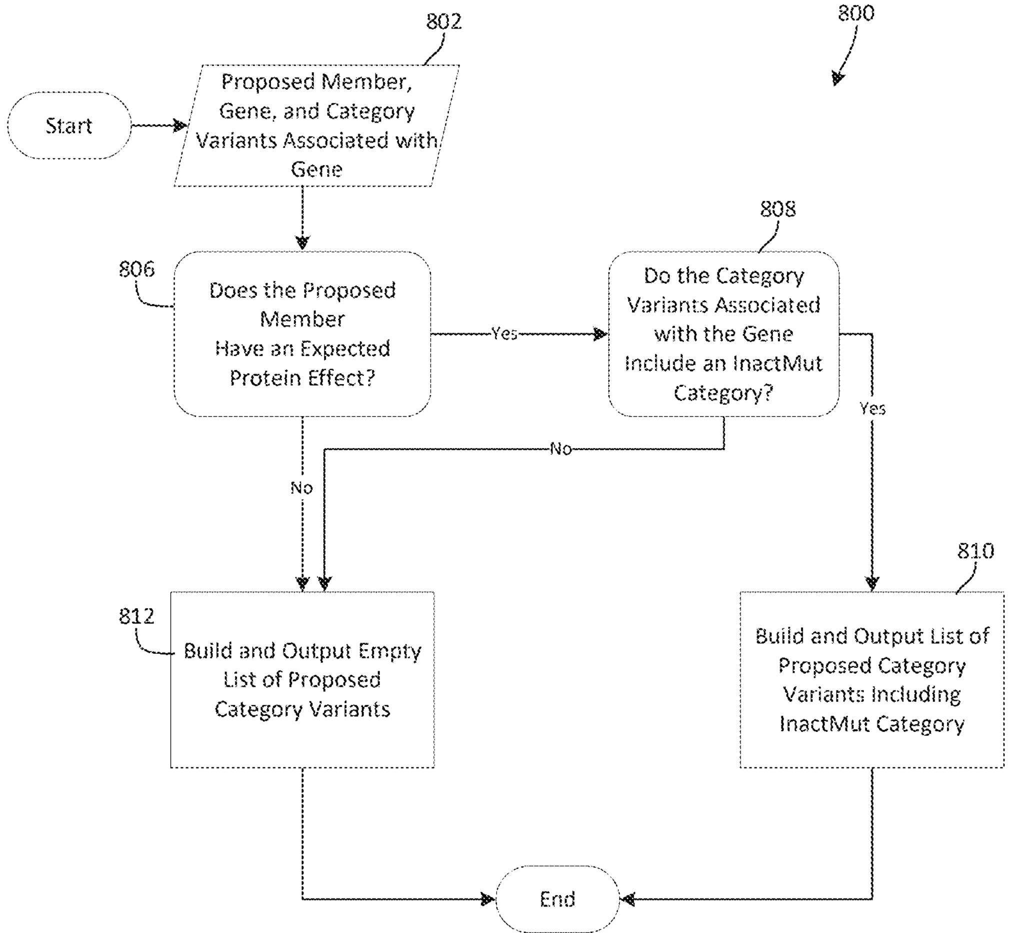
FIG. 8 illustrates a block diagram of a process for applying an InactMut rule, in accordance with some embodiments described herein.

FIG. 8 illustrates a block diagram of a process 800 for applying an InactMut Rule, in accordance with some embodiments described herein. In some embodiments, the InactMut Rule may be applied to a gene variant by the variant category engine of FIG. 2 (e.g., as InactMut Rule 215) or may be implemented independently by any suitable computing device (e.g., the computing device 2000 as described in connection with FIG. 20). In some embodiments, the computing device may pass information 802 to the InactMut Rule including the proposed member (e.g., a gene variant, a category variant, or any other suitable group) and all information associated with the proposed (e.g., location, protein effects, associated treatments), the gene group associated with the proposed member, and a list of category variants associated with the gene group.

In some embodiments, the computing device may begin at act 806 where the computing device may determine whether the proposed member has an expected protein effect that is considered inactivating (e.g., causing a "loss of function"). For example, the computing device may evaluate the information associated with the proposed member and determine whether the information includes information indicative of an inactivating protein effect. Alternatively or additionally, the computing device may compare the information associated with the proposed member with a list of known activating protein effects and determine whether the information includes one or more of the known inactivating protein effects.

If the computing device determines that the proposed member is associated with information indicative of an inactivating protein effect at act 806, then the computing device may proceed 808, in some embodiments. At act 808, the computing device may determine whether the list of category variants associated with the gene provided at 802 include an inact mut ("inactivating mutation") category. In some embodiments, the computing device may also determine, at act 808, whether the proposed member is the inact mut category variant (e.g., if the proposed member is the owner of the inact mut category variant group). If the computing device determines that the list of category variants includes an inact mut category, then the computing device may proceed to act 810 and build and output a list of proposed category variants including the one or more inact mut categories found in the list of category variants associated with the gene.

In some embodiments, if the computing devices determines that the proposed member does not have an activating protein effect at act 806 or does not find an associated inact mut category at act 808, then the computing device will proceed to act 812. At act 812, the computing device may build and output an empty list.

In some embodiments, after the computing device has built a list of proposed category variants in act 810 or after the computing device has built an empty list in act 812, the computing device may output the generated list. The computing device may output the list by communicating it to a system operator in any suitable manner (e.g., displaying on a screen, transmitting to another computing device, etc.). Alternatively or additionally, the computing device may store the list in computer memory for later use (e.g., for later use by the variant category engine 210 to build the initial category variant list). Alternatively or additionally, the computing device may output the list by passing the list to another rule within the variant category engine 210.

Figure 9:
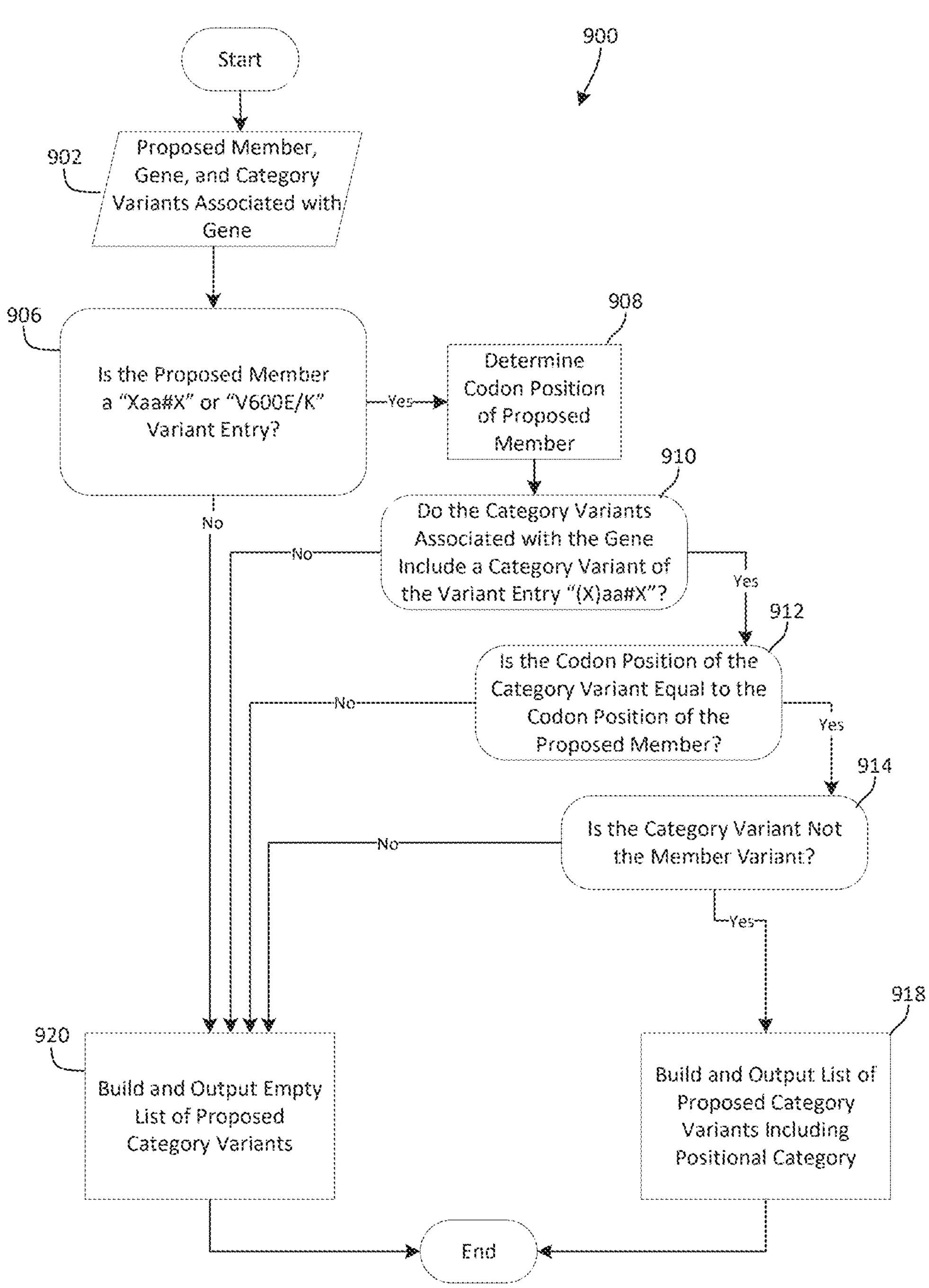
FIG. 9 illustrates a block diagram of a process for applying a positional rule, in accordance with some embodiments described herein.

FIG. 9 illustrates a block diagram of a process 900 for applying a Positional Rule, in accordance with some embodiments described herein. In some embodiments, the Positional Rule may be applied by the variant category engine 210 of FIG. 2 (e.g., as Positional Rule 216) or may be implemented independently by any suitable computing device (e.g., the computing device 2000 as described in connection with FIG. 20). In some embodiments, the computing device may pass information 902 to the Positional Rule including the proposed member (e.g., a gene variant, a category variant, or any other suitable group) and all information associated with the proposed (e.g., location, protein effects, associated treatments), the gene group associated with the proposed member, and a list of category variants associated with the gene group.

In some embodiments, the computing device may begin at act 906 by determining if the proposed member is an "Xaa #X," V600E, or V600K variant entry. An Xaa #X positional mutation is a point mutation where an amino acid has replaced the reference amino acid within a protein. The first "X" represents the reference or wild-type protein that would typically be present at the position "aa #," and the second "X" represents the replacement amino acid found in the gene variant. The computing device may determine that the proposed member is such a positional variant by evaluating the information associated with the proposed member (e.g., the gene or category variant name or regex, in some embodiments) and determining whether the information indicates that the proposed member is a positional mutation.

In some embodiments, if the computing device determines that the proposed member is a positional variant entry, the computing device may proceed to act 908 where the computing device may determine the codon position of the proposed member. In some embodiments, the computing device may extract the codon position from the proposed member's name or regex. For example, if the proposed member is the KRAS G12X variant, the computing device may extract "12" from the proposed member's regex and determine that the variant is associated with the codon position 12.

After determining the proposed member's codon position, the computing device may proceed to act 910 where the computing device may determine whether the category variants associated with the gene provided at 902 include a category variant having a variant entry of the form "(X)aa #X." If the computing device determines that the list includes a category variant having a variant entry of the form "(X)aa #X," then the computing device may proceed to act 912 in some embodiments.

In act 912, the computing device may determine whether the codon position of the category variant is equal to the codon position of the proposed member, in some embodiments. If the computing device determines that the codon position of the category variant is equal to the codon position of the proposed member, then the computing device may proceed to act 914, where the computing device may determine whether the category variant is not the positional category variant (e.g., whether the category variant is not an owner of the positional category variant group).

If the computing device determines at act 914 that the category variant is not the positional category member variant, then the computing device may proceed to act 918, in some embodiments. At act 918, the computing device may build and output a list of proposed category variants to be associated with the proposed member, the list including the determined one or more positional categories from act 910.

In some embodiments, if the computing device determines that the proposed member is not an "Xaa #X," "V600E," or "V600K" variant entry at act 906, then the computing device may instead proceed to act 920 and build and output an empty list. Alternatively or additionally, if the computing device determines that the category variant of the variant entry is not "Xaa #X" at act 910, that the codon position of the category variant is not equal to the codon position of the proposed member at act 912, that the category variant is not a member variant of a positional category at act 914, or that there are no positional category variants present in the list of category variants associated with the gene at act 910, then the computing device may proceed to act 920 and build and output an empty list.

In some embodiments, after the computing device has built a list of proposed category variants in act 918 or after the computing device has built an empty list in act 920, the computing device may output the generated list. The computing device may output the list by communicating it to a system operator in any suitable manner (e.g., displaying on a screen, transmitting to another computing device, etc.). Alternatively or additionally, the computing device may store the list in computer memory for later use (e.g., for later use by the variant category engine 210 to build the initial category variant list). Alternatively or additionally, the computing device may output the list by passing the list to another rule within the variant category engine 210.

Figure 10:
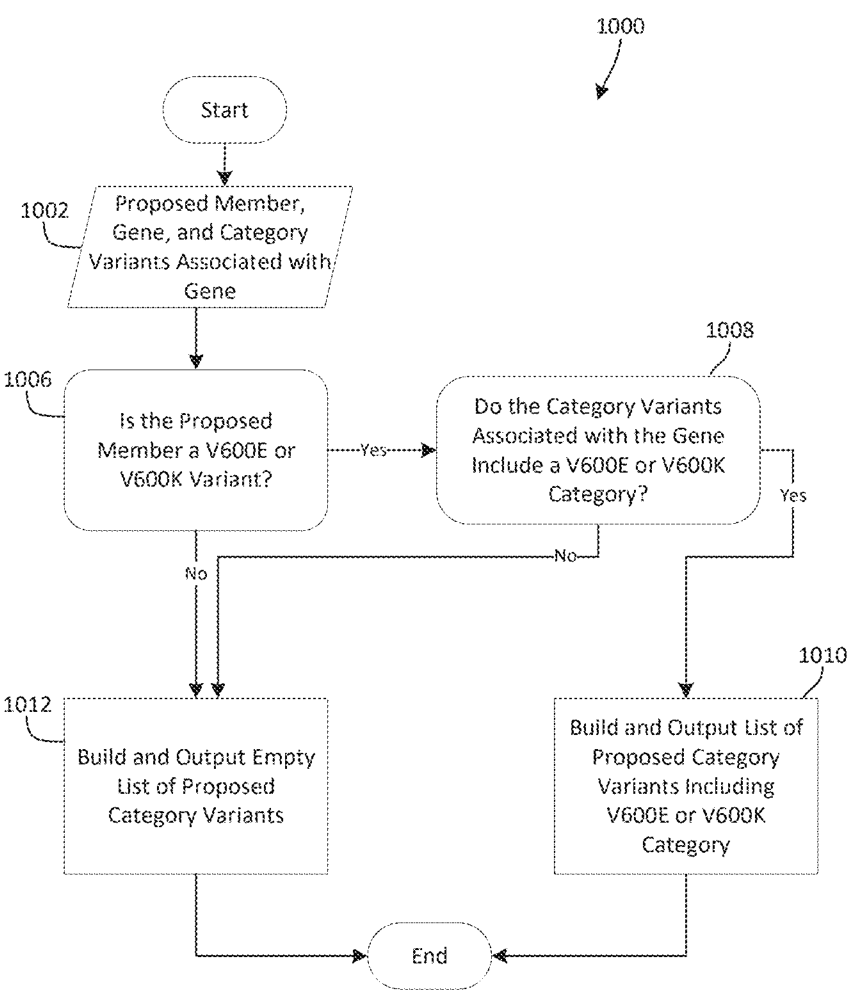
FIG. 10 illustrates a block diagram of an example of a process for applying a special gene rule for BRAF mutations, in accordance with some embodiments described herein.

FIG. 10 illustrates a block diagram of an example of a process 1000 for applying a Special Gene Rule, in accordance with some embodiments described herein. The Special Gene Rule may allow for categorization of special or edge case rules that don't apply to all gene variants or genes. In some embodiments, the Special Gene Rule may be applied to a gene variant by the variant category engine 210 of FIG. 2 (e.g., as Special Gene Rule 217) or may be implemented independently by any suitable computing device (e.g., the computing device 2000 as described in connection with FIG. 20). In some embodiments, the computing device may pass information 1002 to the Special Gene Rule including the proposed member (e.g., a gene variant, a category variant, or any other suitable group) and all information associated with the proposed (e.g., location, protein effects, associated treatments), the gene group associated with the proposed member, and a list of category variants associated with the gene group.

As an example, and in some embodiments, the Special Gene Rule may be configured to categorize V600E and V600K variants of BRAF cancers. In such embodiments, the computing device may first determine whether the proposed member from 1002 is a V600E or V600K genetic variant at act 1006. For example, the computing device may determine whether information associated with the proposed member specifies that the proposed member is a V600E or V600K genetic variant by evaluating the information associated with the proposed member (e.g., by querying the regex and/or other information associated with the proposed member).

If the computing device determines that the proposed member is a genetic mutation of the types V600E or V600K, the computing device may proceed to act 1008, where the computing device may determine whether the list of category variants associated with the gene from 1002 include a V600E or V600K category. If the computing device determines that the proposed category variants include a V600E or V600K category at act 1008, the computing device may proceed to act 1010 where the computing device may build and output a list of proposed category variants including the V600E or V600K category found in act 1008.

In some embodiments, when the computing device determines that the proposed member is not a V600E or V600K variant at act 1006 or the computing device determines that the list of category variants does not include a V600E or V600K category at act 1008, the computing device may proceed to act 1012. At act 1012, the computing device may build and output an empty list. In some embodiments, after the computing device has built a list of proposed category variants in act 1010 or after the computing device has built an empty list in act 1012, the computing device may output the generated list. The computing device may output the list by communicating it to a system operator in any suitable manner (e.g., displaying on a screen, transmitting to another computing device, etc.). Alternatively or additionally, the computing device may store the list in computer memory for later use (e.g., for later use by the variant category engine 210 to build the initial category variant list). Alternatively or additionally, the computing device may output the list by passing the list to another rule within the variant category engine 210.

Figure 11:
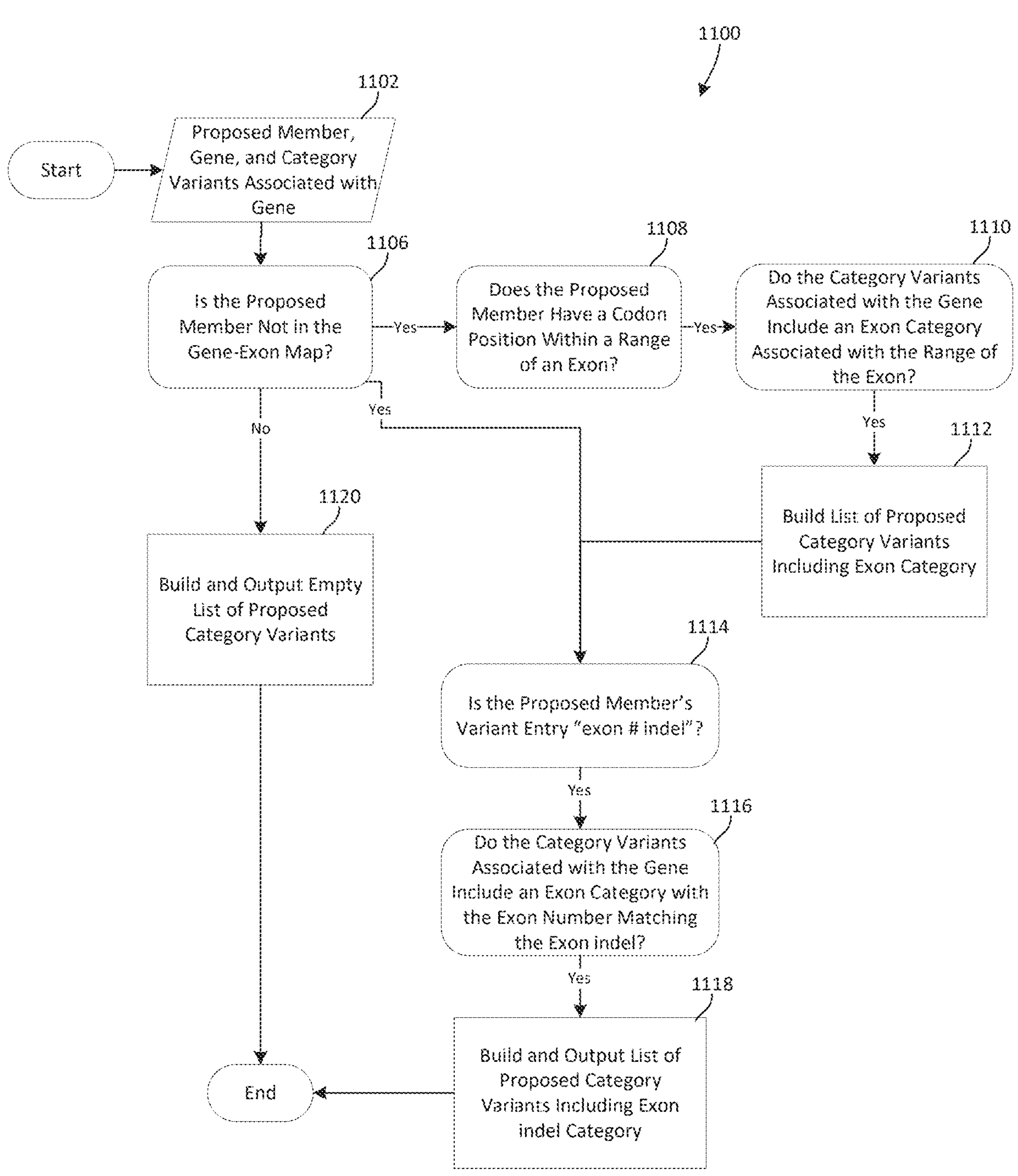
FIG. 11 illustrates a block diagram of a process for applying an exon rule, in accordance with some embodiments described herein.

FIG. 11 illustrates a block diagram of a process 1100 for applying an Exon Rule, in accordance with some embodiments described herein. In some embodiments, the Exon Rule may be applied to a gene variant by the variant category engine 210 of FIG. 2 (e.g., as Exon Rule 218) or may be implemented independently by any suitable computing device (e.g., the computing device 2000 as described in connection with FIG. 20). In some embodiments, the computing device may pass information 1102 to the Exon Rule including the proposed member (e.g., a gene variant, a category variant, or any other suitable group) and all information associated with the proposed (e.g., location, protein effects, associated treatments), the gene group associated with the proposed member, and a list of category variants associated with the gene group.

In some embodiments, the computing device may begin at act 1106 by determining whether the proposed member is not in the gene-exon map. The computing device may make this determination by querying the gene-exon map, which is a data structure including information correlating exons to their positional ranges within the protein. The computing device may compare the position of the proposed member with the positional ranges of the gene-exon map to determine whether the proposed member is located on an exon within the gene-exon map. If the computing device determines that the proposed member is in the gene-exon map, then the computing device may proceed to act 1120, where it builds and outputs an empty list of proposed category variants. For ease of drawing FIG. 11, arrows have been omitted extending from acts 1108, 1110, and 1114 where the computing device has made a determination of "No" and proceeds to act 1120.

In some embodiments, if the computing device determines that the proposed member is not in the gene-exon map at act 1106, it may proceed first to act 1108. At act 1108, the computing device may determine whether the proposed member has a codon position within a range of an exon (e.g., by comparing the codon position of the proposed member with the codon positions of the exons listed in the gene-exon map).

In some embodiments, if the computing device determines that the proposed member has a codon position within a codon position range of an exon in the gene-exon map, then the computing device may proceed to act 1110, where the computing device may determine whether the list of category variants associated with the gene from 1102 include an exon category associated with the codon position range of the exon in the gene-exon map. For example, the computing device may query the list of category variants associated with the gene and determine whether one or more category variants are an exon category and may query the codon position ranges of the category variants that are exon categories to compare the codon position ranges with the range of the exon determined in act 1108. In some embodiments, if the computing device determines in act 1110 that the list of category variants associated with the gene include an exon category variant with a matching codon position range, then the computing device may proceed to act 1112, where the computing device may build a list of proposed category variants including the exon category variant determined in act 1110.

Thereafter, the computing device may proceed to act 1114, where the computing device may determine whether the proposed member's variant entry is an "exon #indel" variant entry. The computing device may make this determination by querying the information associated with the proposed member (e.g., by querying the regex information or other information associated with the proposed member).

In some embodiments, if the computing device determines that the proposed member has an "exon #indel" variant entry, the computing device may proceed to act 1116, where the computing device may determine whether the list of category variants associated with the gene include an exon number matching the exon indel number. The computing device may make this determination by making a comparison of the information associated with the proposed member and the information associated with the category variants of the list of category variants.

In some embodiments, if the computing device determines that the list of category variants includes an exon category with a matching exon indel number, then the computing device may proceed to act 1118. At act 1118, the computing device may build a list of proposed category variants including the exon indel category. In some embodiments, the list may be built by appending the list to the list that was built at act 1112, but in other embodiments these two lists may be built separately. In some embodiments, if the computing device determines that there are no category variants in the list of category variants with a matching exon indel number, then the computing device may build or append an empty list.

In some embodiments, after the computing device has built a list of proposed category variants in act 1118 or after the computing device has built an empty list in act 1120, the computing device may output the generated list. The computing device may output the list by communicating it to a system operator in any suitable manner (e.g., displaying on a screen, transmitting to another computing device, etc.). Alternatively or additionally, the computing device may store the list in computer memory for later use (e.g., for later use by the variant category engine 210 to build the initial category variant list). Alternatively or additionally, the computing device may output the list by passing the list to another rule within the variant category engine 210.

Figure 12:
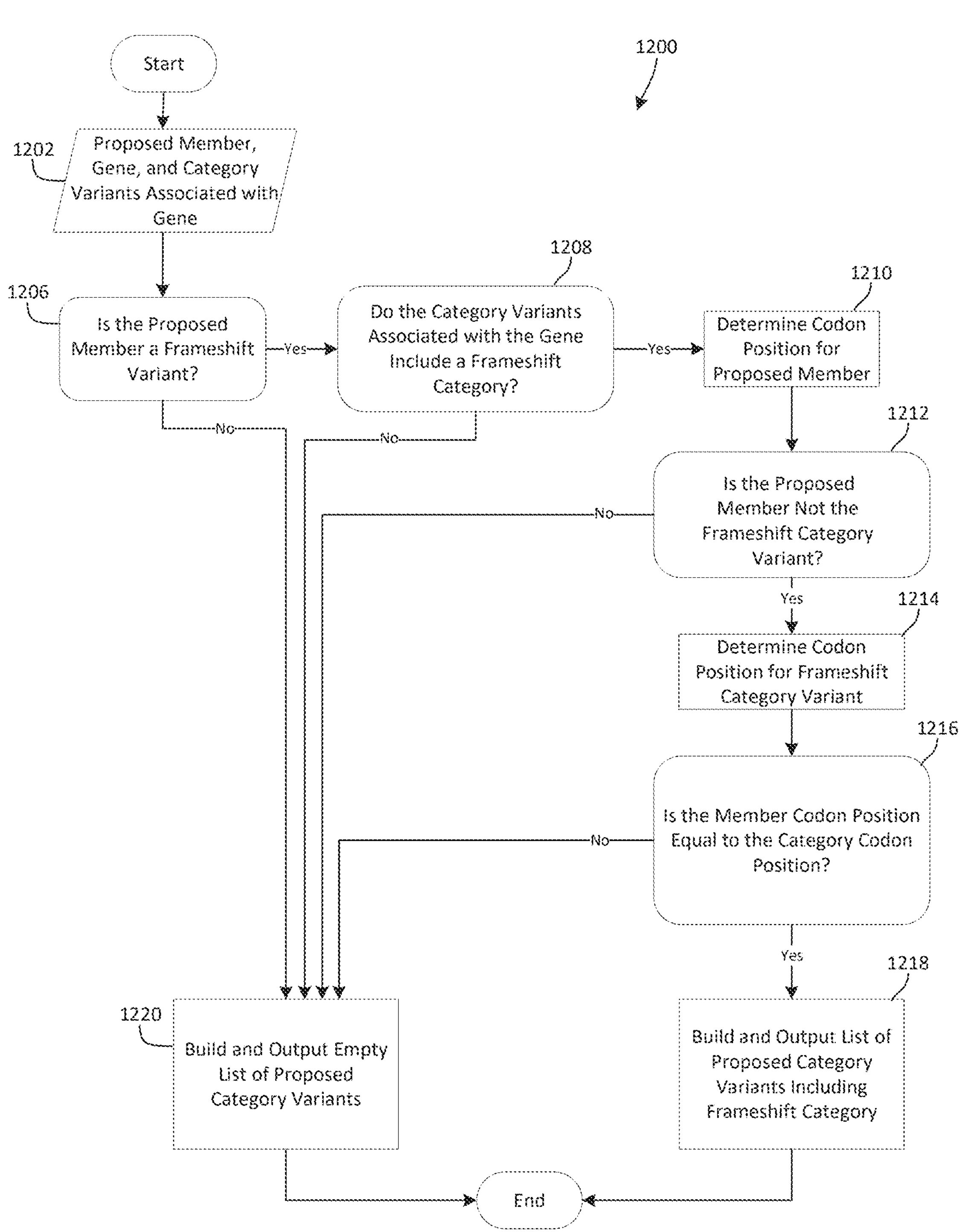
FIG. 12 illustrates a block diagram of a process for applying a frameshift rule, in accordance with some embodiments described herein.

FIG. 12 illustrates a block diagram of a process 1200 for applying a Frameshift Rule, in accordance with some embodiments described herein. In some embodiments, the Frameshift Rule may be applied to a genetic variant by the variant categorization engine 210 of FIG. 2 (e.g., as Frameshift Rule 219) or may be implemented independently by any suitable computing device (e.g., the computing device 2000 as described in connection with FIG. 20). In some embodiments, the computing device may pass information 1202 to the Frameshift Rule including the proposed member (e.g., a gene variant, a category variant, or any other suitable group) and all information associated with the proposed (e.g., location, protein effects, associated treatments), the gene group associated with the proposed member, and a list of category variants associated with the gene group.

In some embodiments, the computing device may begin at act 1206 by determining whether the proposed member is a frameshift variant. For example, the computing device may determine whether the information associated with the proposed member indicates that the proposed member is a frameshift variant (e.g., in the regex or other information). If the computing device determines that the proposed member is a frameshift variant, then the computing device may proceed to act 1208 where the computing device may determine whether the list of category variants associated with the gene includes a frameshift category.

In some embodiments, the computing device may determine whether the list of category variants associated with the gene includes a frameshift category by querying information associated with each category variant in the list. For example, the computing device may query regex or other information associated with each category variant in the list to determine if the list includes a frameshift category variant.

If the computing device determines that the list of category variants includes a frameshift category, then the computing device may proceed to act 1210. In some embodiments, at act 1210 the computing device may determine the codon position for the proposed member (e.g., as described in connection with act 908 of FIG. 9 herein).

After determining the codon position of the proposed member, the computing device may proceed to act 1212, where the computing device may determine whether the proposed member is not the frameshift category variant (e.g., not the owner of a frameshift category variant group). In some embodiments, if the computing device determines that the proposed member is not the frameshift category variant, the computing device may proceed to act 1214 where the computing device determines the codon position for the frameshift category variant (e.g., by extracting the codon position from the information associated with the category variant).

In some embodiments, the computing device may then proceed to act 1216, where the computing device may determine whether the codon position of the proposed member is equal to the codon position of the category variant. For example, the computing device may compare the codon position values to make this determination. If the computing device determines that the codon positions are equal in act 1216, then the computing device may proceed to act 1218 where it builds and outputs a list of category variants including the frameshift category with the matching codon position from act 1216.

In some embodiments, after the computing device has built a list of proposed category variants in act 1218 or after the computing device has built an empty list in act 1220, the computing device may output the generated list. The computing device may output the list by communicating it to a system operator in any suitable manner (e.g., displaying on a screen, transmitting to another computing device, etc.). Alternatively or additionally, the computing device may store the list in computer memory for later use (e.g., for later use by the variant category engine 210 to build the initial category variant list). Alternatively or additionally, the computing device may output the list by passing the list to another rule within the variant category engine 210.

In some embodiments, when the computing device determines that the proposed member is not a frameshift variant at act 1206, or that the list of category variants do not include a frameshift category at act 1208, or that the proposed member is a variant from the frameshift category at act 1212, or that the codon positions of the proposed member and the category do not match at act 1216, the computing device may proceed to act 1220. At act 1220, the computing device may build and output an empty list.

In some embodiments, after the computing device has built a list of proposed category variants in act 1218 or after the computing device has built an empty list in act 1220, the computing device may output the generated list. The computing device may output the list by communicating it to a system operator in any suitable manner (e.g., displaying on a screen, transmitting to another computing device, etc.). Alternatively or additionally, the computing device may store the list in computer memory for later use (e.g., for later use by the variant category engine 210 to build the initial category variant list). Alternatively or additionally, the computing device may output the list by passing the list to another rule within the variant category engine 210.

Figure 13A:
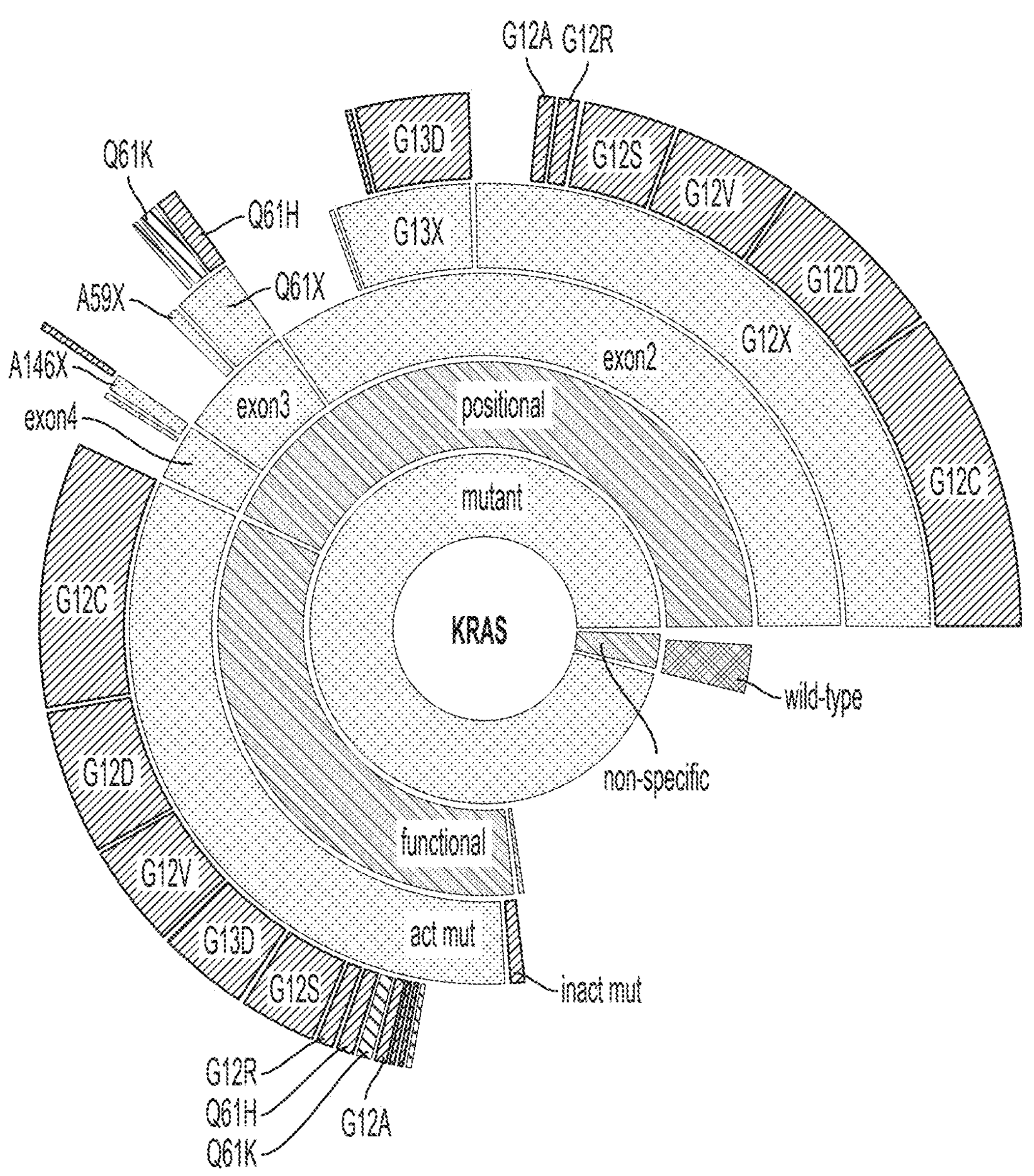
FIGS. 13A and 13B are examples of a plot generated for the KRAS gene and the positional category of the KRAS gene, respectively, in accordance with some embodiments described herein.
Figure 13B:
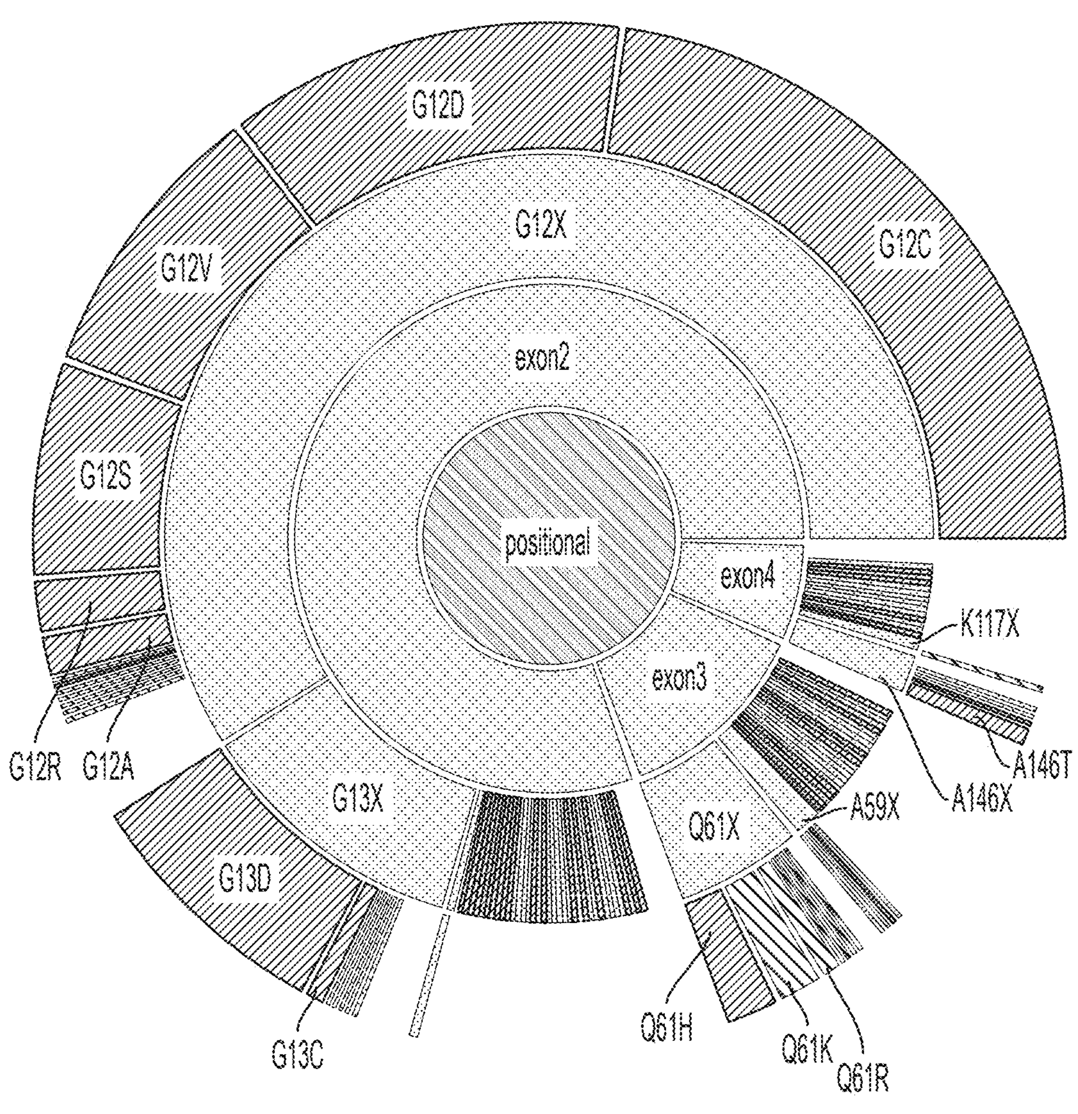

FIG. 13A is an example of a sunburst plot generated for the KRAS gene using the hierarchical gene variant categorizations determined using the variant categorization engine 210 of FIG. 2, in accordance with some embodiments herein. FIG. 13B is an example of a sunburst plot generated for the positional category of the KRAS gene, in accordance with some embodiments described herein. FIG. 13A shows a sunburst plot describing the groupings of category types and gene variants for the KRAS gene. As can be seen from FIG. 13A, the KRAS gene variants may first, in the inner ring, be classified into either "mutant" or "non-specific" categories. The gene variants of the mutant category may further be sub-categorized into sub-groups of "functional" or "positional" category variants in the second inner ring.

In some embodiments, a practitioner may navigate between the different category variants of these sunburst plots by clicking on portions of the rings within the sunburst plots. For example, a practitioner may navigate to the sunburst plot of FIG. 13B by clicking on the "positional" portion of the second inner ring of FIG. 13A. By navigating to FIG. 13B, the practitioner may obtain a more detailed view of the positional category variants of the KRAS gene. For example, FIG. 13B shows further sub-categorizations of the positional category, including exon categories exon 2, exon4, and exon3. As an example of the way a gene variant is categorized, the G12C gene variant belongs to the following hierarchical chain of groupings, as pictured in FIGS. 13A and 13B: KRAS>mutant>functional>act mut>G12C and KRAS>mutant>positional>exon2>G12X>G12C.

Figure 14A:
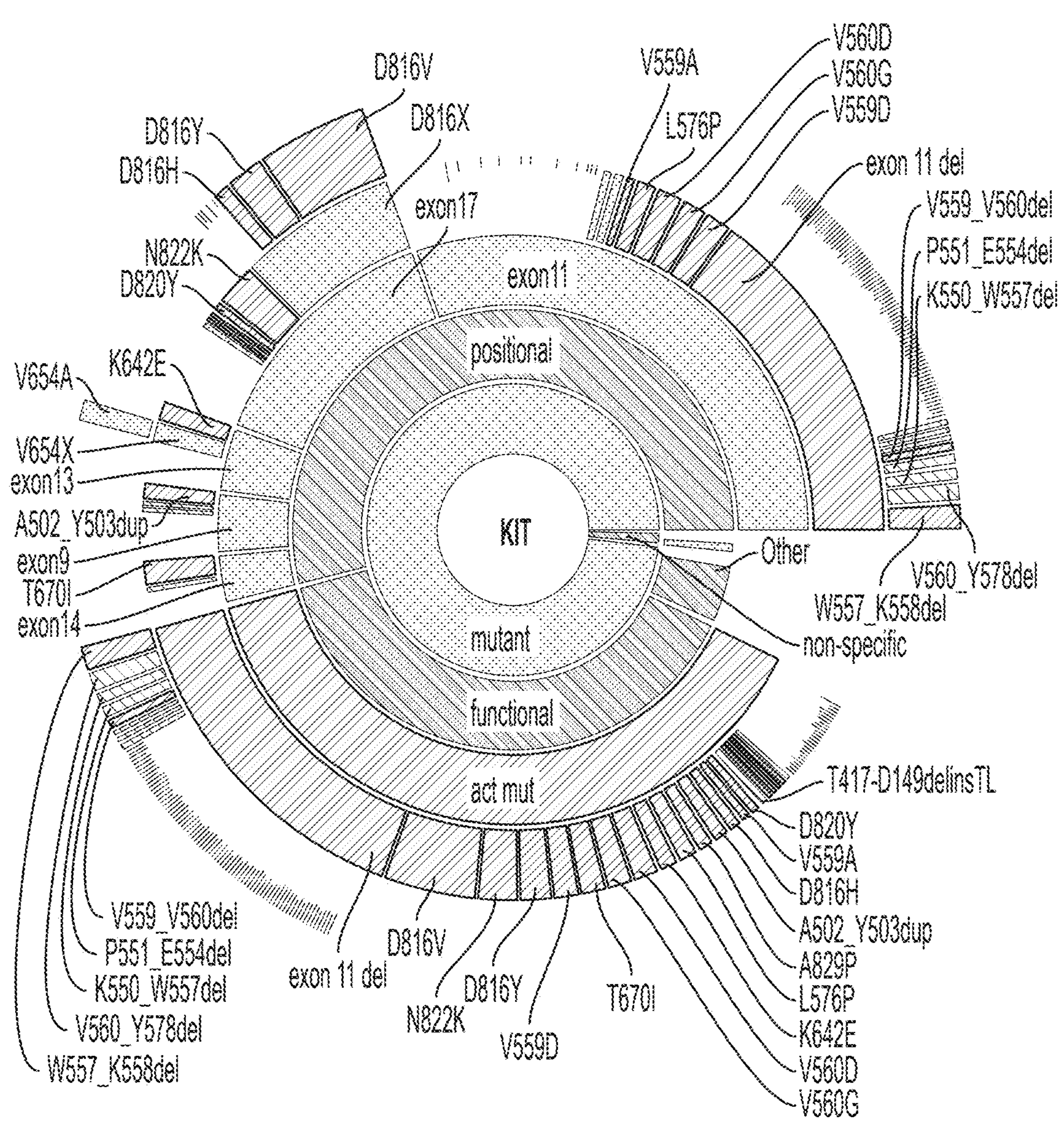
FIGS. 14A and 14B are examples of a plot generated for the KIT gene and the exon 11 deletion category of the KIT gene, respectively, in accordance with some embodiments described herein.
Figure 14B:
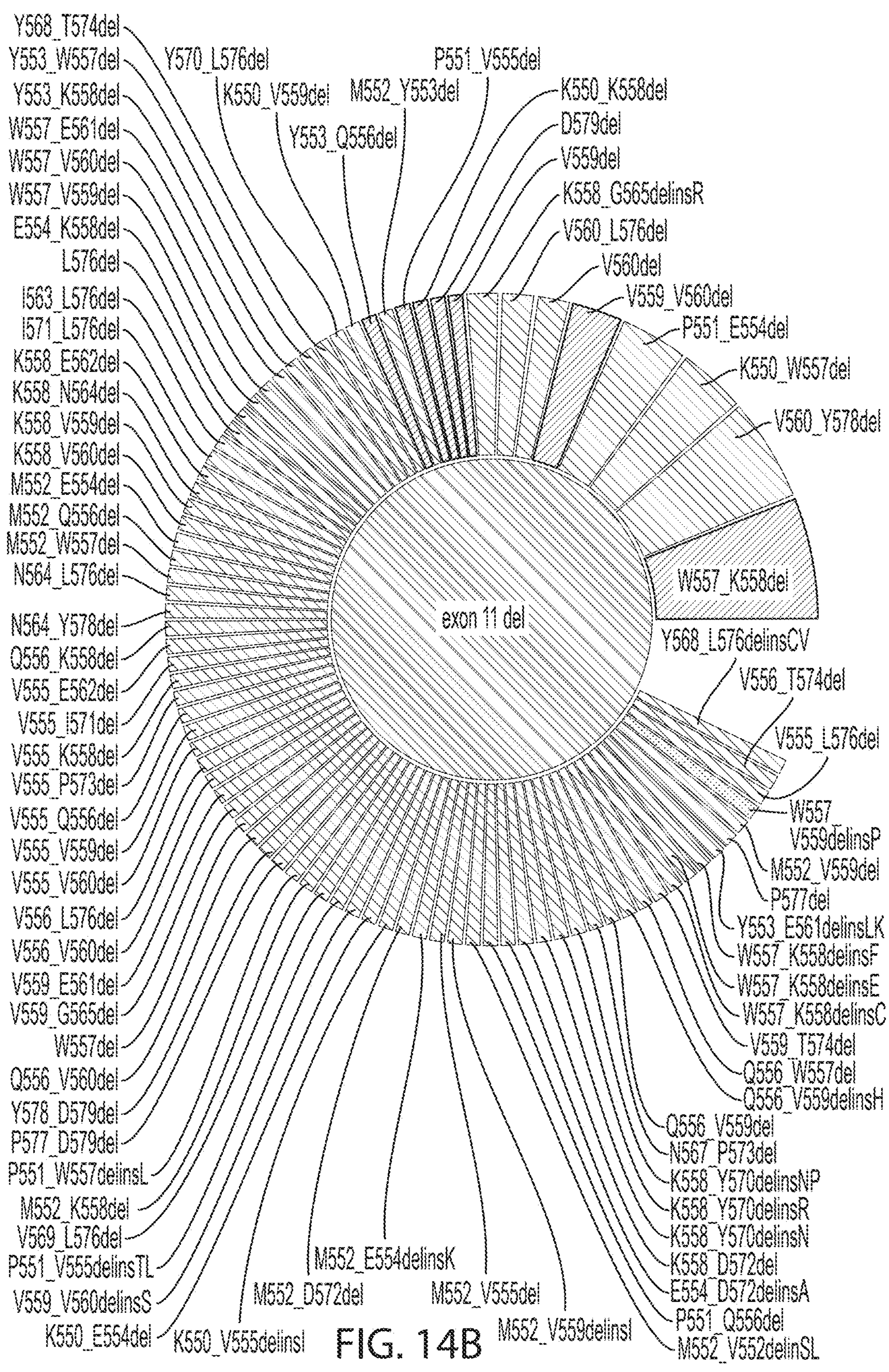

FIG. 14A is an example of a sunburst plot generated for the KIT gene using the hierarchical gene variant categorization methods described herein. FIG. 14B is an example of a sunburst plot for the exon 11 deletion category of the KIT gene, in accordance with some embodiments described herein. As can be seen from FIG. 14A, the KIT gene variants may first be classified into either "mutant" or "non-specific" categories. The gene variants of the mutant category may further be categorized into sub-groups of "functional," "positional," or "other."

In some embodiments, a practitioner may navigate to more detailed plots of specific category variants. For example, the practitioner may navigate to FIG. 14B by clicking on the "exon11" portion of FIG. 14A. FIG. 14B provides a more detailed plot including all gene variants associated with the exon11 category. As an example of this categorization, the W557_K558del gene variant belongs to the following hierarchical chain of groupings, as pictured in FIGS. 14A and 14B: KIT>mutant>positional>exon11>exon11del>W557_K558del. The visualizations of FIGS. 13A, 13B, 14A, and 14B provide a holistic way to navigate the families of gene variants.

Figure 15:
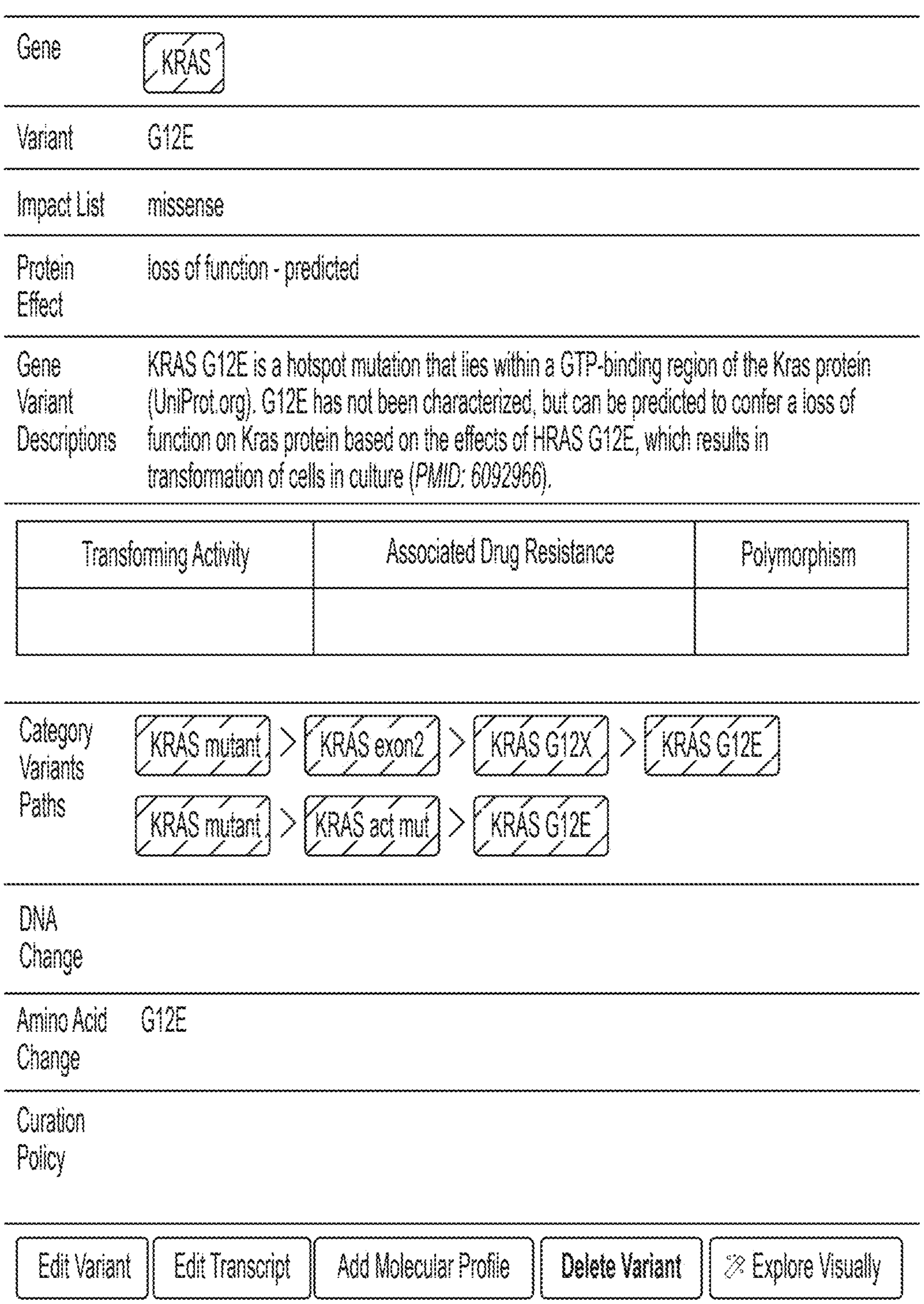
FIG. 15 illustrates an example of a user interface displaying information related to the KRAS gene variant, KRAS G12E, in accordance with some embodiments described herein.

In addition to the sunburst plots of FIGS. 13A, 13B, 14A, and 14B, additional information relating to the category variants may be displayed in the user interface. For example, the user interface may display information relating information about treatment modalities (e.g., FDA-approved treatments, phase I or II clinical trial results, and/or clinical trial recruitment information) associated with a category variant. FIG. 15 illustrates an example of such a user interface and displays information related to the G12E gene variant of the KRAS gene, in accordance with some embodiments described herein. When a user accesses a gene variant, the system may display information such as the parent gene (e.g., KRAS in the example of FIG. 15), the protein effect of the gene variant, any associated description, and category paths.

FIG. 16 illustrates an example of a user interface displaying further information related to the G12E gene variant of the KRAS gene and its relation to cancer therapies, in accordance with some embodiments described herein. When a user accesses a gene variant through the user interface, the system may display information detailing the relationship between the gene variant and treatment options in the "Extended Evidence" tab, which has been selected in the example of FIG. 16. Such information may include related treatment or therapy names, the response of a cancer having the gene variant to the treatment, and further information about the evidence supporting the response of the cancer to the treatment (e.g., information regarding case studies, Phase I trials, etc.).

FIG. 17 illustrates an example of a user interface configured to allow a user to review gene variants whose stored category memberships do not match those of the variant category engine, in accordance with some embodiments described herein. The system may provide a user interface, such as shown in FIG. 17, to allow the user to easily confirm such category memberships and compare them against the system's predicted categorizations based on the applied rules and groupings as described herein. The system may provide this user interface, for example, at act 122 as described in connection with FIG. 1B herein.

FIG. 18 illustrates an example of a user interface displaying gene variant categories related to the KRAS gene, in accordance with some embodiments described herein. In some embodiments, a user may view information related to the category groupings associated with a gene as in the example of FIG. 18 in addition to a visualization (e.g., as in FIGS. 13-14). The category groupings may be shown alongside category paths, the type of gene variant, and/or protein effects of gene variants within the category grouping.

Figure 19A:
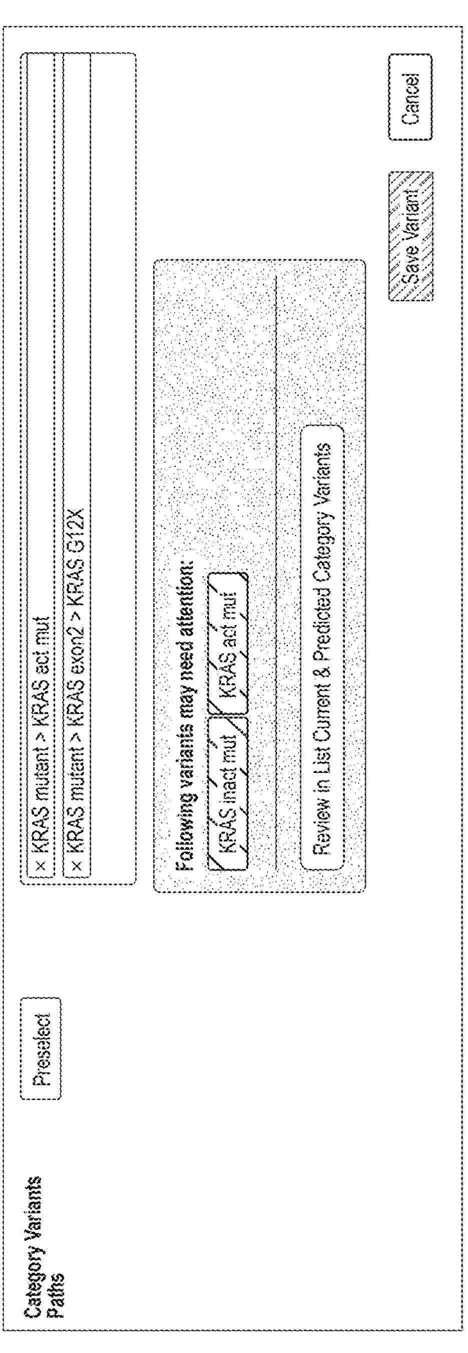
FIG. 19A illustrates an example of a user interface configured to enable a user to edit categories associated with a gene variant, in accordance with some embodiments described herein.

FIG. 19A illustrates an example of a user interface configured to enable a user to edit information related to a gene variant, in accordance with some embodiments described herein. In some embodiments, a user may wish to update information stored in the system regarding a gene or gene variant (e.g., in response to new research). The system may provide a user interface for updating this information, including updating category group paths.

FIG. 19B illustrates an example of a user interface configured to display differences between a user's selection of categories associated with a gene variant and predicted categories, in accordance with some embodiments described herein. As shown in the example of FIG. 19B, the user has selected for the KRAS G12E variant a series of category variants under the "Selected Category Variants" tab that do not match the category variants generated by the variant category engine and listed under the "Predicted Category Variants" tab. The user interface shows a warning symbol in the "Current & Predicted Category Variants" tab to indicate that the user's selections and the engine's predictions do not match.

FIG. 19C illustrates an example of a user interface configured to enable a user to edit information related to a category, in accordance with some embodiments described herein. In some embodiments, a user may wish to update information stored in the system regarding a category (e.g., in response to new research). The system may provide a user interface for updating this information, the user interface including means to update category variant paths for the category itself and a list of category members which may further need to be updated.

FIG. 20 shows, schematically, an illustrative computer 2000 on which any aspect of the present disclosure may be implemented. For example, the variant category engine as described herein may be implemented using computer 2000, or any other suitable computing device and/or distributed computing device. The computer 2000 includes a processing unit 2001 having one or more processors and a non-transitory computer-readable storage medium 2002 that may include, for example, volatile and/or non-volatile memory. The memory 2002 may store one or more instructions to program the processing unit 2001 to perform any of the functions described herein. The computer 2000 may also include other types of non-transitory computer-readable medium, such as storage 2005 (e.g., one or more disk drives) in addition to 20 the system memory 2002. The storage 2005 may also store one or more application programs and/or resources used by application programs (e.g., software libraries), which may be loaded into the memory 2002.

The computer 2000 may have one or more input devices and/or output devices, such as devices 2006 and 2007 illustrated in FIG. 20. These devices may be used, for instance, to present a user interface. Examples of output devices that may be used to provide a user interface include printers and display screens for visual presentation of output, and speakers and other sound generating devices for audible presentation of output. Examples of input devices that may be used for a user interface include keyboards and acting devices (e.g., mice, touch pads, and digitizing tablets). As another example, the input devices 2007 may include a microphone for capturing audio signals, and the output devices 2006 may include a display screen for visually rendering, and/or a speaker for audibly rendering, recognized text.

In the example shown in FIG. 20, the computer 2000 also includes one or more network interfaces (e.g., the network interface 2010) to enable communication via various networks (e.g., the network 2020). Examples of networks include a local area network (e.g., an enterprise network) and a wide area network (e.g., the Internet). Such networks may be based on any suitable technology and operate according to any suitable protocol, and may include wireless networks and/or wired networks (e.g., fiber optic networks).

Further description of the embodiments described above can be found in the Appendix herein, which forms a part of the application and is fully incorporated herein by reference.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Further, though advantages of the present invention are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semi-custom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Also, the various methods or processes outlined herein may be coded as software that is executable on one or more processors running any one of a variety of operating systems or platforms. Such software may be written using any of a number of suitable programming languages and/or programming tools, including scripting languages and/or scripting tools. In some instances, such software may be compiled as executable machine language code or intermediate code that is executed on a framework or virtual machine. Additionally, or alternatively, such software may be interpreted.

The techniques disclosed herein may be embodied as a non-transitory computer-readable medium (or multiple computer-readable media) (e.g., a computer memory, one or more floppy discs, compact discs, optical discs, magnetic tapes, flash memories, circuit configurations in Field Programmable Gate Arrays or other semiconductor devices, or other non-transitory, tangible computer storage medium) encoded with one or more programs that, when executed on one or more processors, perform methods that implement the various embodiments of the present disclosure discussed above. The computer-readable medium or media may be transportable, such that the program or programs stored thereon may be loaded onto one or more different computers or other processors to implement various aspects of the present disclosure as discussed above.

The terms "program" or "software" are used herein to refer to any type of computer code or set of computer-executable instructions that may be employed to program one or more processors to implement various aspects of the present disclosure as discussed above. Moreover, it should be appreciated that according to one aspect of this embodiment, one or more computer programs that, when executed, perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Program modules may include routines, programs, objects, components, data structures, etc. that perform particular tasks or implement particular abstract data types. Functionalities of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields to locations in a computer-readable medium that convey relationship between the fields. However, any suitable mechanism may be used to establish a relationship between information in fields of a data structure, including through the use of acters, tags, or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The described technology may be embodied in the following configurations:

(1) A method for determining relationships between gene variants of a gene, the gene variants being related to one or more cancers and being correlated to a treatment response of the one or more cancers to one or more treatments, the method comprising: accessing, using at least one processor, a database comprising information about the gene variants, the information including at least information indicative of a treatment response of a first gene variant of the gene variants to one or more treatments; categorizing, using the at least one processor, the information about the gene variants within a plurality of groups; and generating, using the at least one processor, hierarchical relationships between each group of the plurality of groups.

(2) The method of (1), further comprising: generating, using the at least one processor, a visualization of the hierarchical relationships between each group of the plurality of groups; and displaying, on a user interface of a computing device, the visualization.

(3) The method of any one of (1)-(2), wherein the act of categorizing further comprises categorizing the information about the gene variants within the plurality of groups such that each member of a group of the plurality of groups is unique.

(4) The method of any one of (1)-(3), wherein categorizing further comprises selecting, based on the categorized information about the gene variants within a group of the plurality of groups, an owner member of the group, wherein the owner member comprises information about a group category.

(5) The method of any one of (1)-(4), wherein the act of generating the hierarchical relationship further comprises generating a directed acyclic graph.

(6) The method of any one of (1)-(5), wherein categorizing, using the at least one processor, the information about the gene variants further comprises: determining, based on information associated with a second gene variant of the gene variants, whether the second gene variant is a specific fusion mutation; and conditionally categorizing, based on determining that the second gene variant is a specific fusion mutation, the second gene variant as a member of a fusion group or a rearrange group by determining whether the information associated with the second gene variant includes information indicating that a gene group including the second gene variant includes a fusion group or a rearrange group.

(7) The method of any one of (1)-(6), wherein categorizing, using the at least one processor, the information about the gene variants further comprises: determining, based on information associated with a second gene variant of the gene variants, whether the second gene variant is a fusion mutation; and conditionally categorizing, based on determining that the second gene variant is a fusion mutation, the second gene variant as a member of a rearrange group by determining whether the information associated with the second gene variant includes information indicating that a gene group including the second gene variant includes a rearrange group.

(8) The method of any one of (1)-(7), wherein categorizing, using the at least one processor, the information about the gene variants further comprises: determining, based on information associated with a second gene variant of the gene variants, whether the second gene variant is a non-specific mutation type; determining, based on the information associated with the second gene variant, whether the second gene variant is a mutant; determining whether the information associated with the second gene variant includes information indicating that a gene group including the second gene variant includes a mutant group; and conditionally categorizing the second gene variant as a member of a mutant group if: (1) the second gene variant is not a non-specific mutation type, (2) the second gene variant is not a mutant, and (3) the information associated with the second gene variant includes information indicating that a gene group including the second gene variant includes a mutant group.

(9) The method of any one of (1)-(8), wherein categorizing, using the at least one processor, the information about the gene variants further comprises: determining, based on information associated with a second gene variant of the gene variants, whether the second gene variant is a gene variant having an activating protein effect; determining whether the information associated with the second gene variant includes information indicating that a gene group including the second gene variant includes an activating mutation (act mut) group; and conditionally categorizing the second gene variant as a member of an act mut group if: (1) the second gene variant is a gene variant having an activating protein effect and (2) the information associated with the second gene variant includes information indicating that a gene group including the second gene variant includes an act mut group.

(10) The method of any one of (1)-(9), wherein categorizing, using the at least one processor, the information about the gene variants further comprises: determining, based on information associated with a second gene variant of the gene variants, whether the second gene variant is a gene variant having an inactivating protein effect; determining whether the information associated with the second gene variant includes information indicating that a gene group including the second gene variant includes an inactivating mutation (inact mut) group; and conditionally categorizing the second gene variant as a member of an inact mut group if: (1) the second gene variant is a gene variant having an inactivating protein effect and (2) the information associated with the second gene variant includes information indicating that a gene group including the second gene variant includes an inact mut group.

(11) The method of any one of (1)-(10), wherein categorizing, using the at least one processor, the information about the gene variants further comprises: determining, based on information associated with a second gene variant of the gene variants, whether the second gene variant is a positional mutation; determining a codon position of the second gene variant based on the information associated with the second gene variant; comparing the determined codon position of the second gene variant with a codon position of a proposed positional group; and conditionally categorizing the second gene variant as a member of the positional group if the determined codon position of the second gene variant is equal to the codon position of the proposed positional group.

(12) The method of any one of (1)-(11), wherein categorizing, using the at least one processor, the information about the gene variants further comprises: determining whether a second gene variant is a V600E or V600K gene variant based on information associated with the second gene variant; determining whether the information associated with the second gene variant includes information indicating that a gene group including the second gene variant includes a V600E or V600K group; conditionally categorizing the second gene variant as a member of a V600E or V600K group if: (1) the second gene variant is a V600E or V600K gene variant and (2) the information associated with the second gene variant includes information indicating that a gene group including the second gene variant includes a V600E or V600K group.

(13) The method of any one of (1)-(12), wherein categorizing, using the at least one processor, the information about the gene variants further comprises: determining, based on information associated with a second gene variant of the gene variants, whether the second gene variant is a part of a gene-exon map; (1) conditionally determining, based on the determination that the second gene variant is a part of the gene-exon map and the information associated with the second gene variant, if a codon position of the second gene variant is within a positional range of an exon in the gene-exon map; (2) conditionally determining, based on the determination that the second gene variant is a part of the gene-exon map, if the information associated with the second gene variant comprises information indicative of the second gene variant belonging to an exon #indel group; and conditionally categorizing, based on affirmative determinations in (1) and/or (2), the second gene variant as a member of an exon group and/or an exon indel group.

(14) The method of any one of (1)-(13), wherein categorizing, using the at least one processor, the information about the gene variants further comprises: determining, based on information associated with a second gene variant, whether a second gene variant of the gene variants is a frameshift gene variant; determining, based on the information associated with the second gene variant, a codon position of a second gene variant; determining a codon position of a proposed frameshift group; and conditionally categorizing the second gene variant as a member of the proposed frameshift group if the codon position of the second gene variant is equal to the codon position of the frameshift group.

(15) A system for determining relationships between gene variants of a gene, the gene variants being related to one or more cancers and being correlated to a treatment response of the one or more cancers to one or more medications, the system comprising: at least one processor; and at least one computer memory storing instructions, that, when executed by the at least one processor, perform a method of: accessing, using at least one processor, a database comprising information about the gene variants, the information including at least information indicative of a treatment response of a first gene variant of the gene variants to one or more treatments; categorizing, using the at least one processor, the information about the gene variants within a plurality of groups; and generating, using the at least one processor, hierarchical relationships between each group of the plurality of groups.

(16) The system of (15), further comprising: generating, using the at least one processor, a visualization of the hierarchical relationships between each group of the plurality of groups; and displaying, on a user interface of a computing device, the visualization.

(17) The system of any one of (15)-(16), wherein the act of categorizing further comprises categorizing the information about the gene variants within the plurality of groups such that each member of a group of the plurality of groups is unique.

(18) The system of any one of (15)-(17), wherein categorizing further comprises selecting, based on the categorized information about the gene variants within a group of the plurality of groups, an owner member of the group, wherein the owner member comprises information about a group category.

(19) The system of any one of (15)-(18), wherein the act of generating the hierarchical relationship further comprises generating a directed acyclic graph.

(20) The system of any one of (15)-(19), wherein categorizing, using the at least one processor, the information about the gene variants further comprises: determining, based on information associated with a second gene variant of the gene variants, whether the second gene variant is a specific fusion mutation; and conditionally categorizing, based on determining that the second gene variant is a specific fusion mutation, the second gene variant as a member of a fusion group or a rearrange group by determining whether the information associated with the second gene variant includes information indicating that a gene group including the second gene variant includes a fusion group or a rearrange group.

(21) The system of any one of (15)-(20), wherein categorizing, using the at least one processor, the information about the gene variants further comprises: determining, based on information associated with a second gene variant of the gene variants, whether the second gene variant is a fusion mutation; and conditionally categorizing, based on determining that the second gene variant is a fusion mutation, the second gene variant as a member of a rearrange group by determining whether the information associated with the second gene variant includes information indicating that a gene group including the second gene variant includes a rearrange group.

(22) The system of any one of (15)-(21), wherein categorizing, using the at least one processor, the information about the gene variants further comprises: determining, based on information associated with a second gene variant of the gene variants, whether the second gene variant is a non-specific mutation type; determining, based on the information associated with the second gene variant, whether the second gene variant is a mutant; determining whether the information associated with the second gene variant includes information indicating that a gene group including the second gene variant includes a mutant group; and conditionally categorizing the second gene variant as a member of a mutant group if: (1) the second gene variant is not a non-specific mutation type, (2) the second gene variant is not a mutant, and (3) the information associated with the second gene variant includes information indicating that a gene group including the second gene variant includes a mutant group.

(23) The system of any one of (15)-(22), wherein categorizing, using the at least one processor, the information about the gene variants further comprises: determining, based on information associated with a second gene variant of the gene variants, whether the second gene variant is a gene variant having an activating protein effect; determining whether the information associated with the second gene variant includes information indicating that a gene group including the second gene variant includes an activating mutation (act mut) group; and conditionally categorizing the second gene variant as a member of an act mut group if: (1) the second gene variant is a gene variant having an activating protein effect and (2) the information associated with the second gene variant includes information indicating that a gene group including the second gene variant includes an act mut group.

(24) The system of any one of (15)-(23), wherein categorizing, using the at least one processor, the information about the gene variants further comprises: determining, based on information associated with a second gene variant of the gene variants, whether the second gene variant is a gene variant having an inactivating protein effect; determining whether the information associated with the second gene variant includes information indicating that a gene group including the second gene variant includes an inactivating mutation (inact mut) group; and conditionally categorizing the second gene variant as a member of an inact mut group if: (1) the second gene variant is a gene variant having an inactivating protein effect and (2) the information associated with the second gene variant includes information indicating that a gene group including the second gene variant includes an inact mut group.

(25) The system of any one of (15)-(24), wherein categorizing, using the at least one processor, the information about the gene variants further comprises: determining, based on information associated with a second gene variant of the gene variants, whether the second gene variant is a positional mutation; determining a codon position of the second gene variant based on the information associated with the second gene variant; comparing the determined codon position of the second gene variant with a codon position of a proposed positional group; and conditionally categorizing the second gene variant as a member of the positional group if the determined codon position of the second gene variant is equal to the codon position of the proposed positional group.

(26) The system of any one of (15)-(25), wherein categorizing, using the at least one processor, the information about the gene variants further comprises: determining whether a second gene variant is a V600E or V600K gene variant based on information associated with the second gene variant; determining whether the information associated with the second gene variant includes information indicating that a gene group including the second gene variant includes a V600E or V600K group; conditionally categorizing the second gene variant as a member of a V600E or V600K group if: (1) the second gene variant is a V600E or V600K gene variant and (2) the information associated with the second gene variant includes information indicating that a gene group including the second gene variant includes a V600E or V600K group.

(27) The system of any one of (15)-(26), wherein categorizing, using the at least one processor, the information about the gene variants further comprises: determining, based on information associated with a second gene variant of the gene variants, whether the second gene variant is a part of a gene-exon map; (1) conditionally determining, based on the determination that the second gene variant is a part of the gene-exon map and the information associated with the second gene variant, if a codon position of the second gene variant is within a positional range of an exon in the gene-exon map; (2) conditionally determining, based on the determination that the second gene variant is a part of the gene-exon map, if the information associated with the second gene variant comprises information indicative of the second gene variant belonging to an exon #indel group; and conditionally categorizing, based on affirmative determinations in (1) and/or (2), the second gene variant as a member of an exon group and/or an exon indel group.

(28) The system of any one of (15)-(27), wherein categorizing, using the at least one processor, the information about the gene variants further comprises: determining, based on information associated with a second gene variant, whether a second gene variant of the gene variants is a frameshift gene variant; determining, based on the information associated with the second gene variant, a codon position of a second gene variant; determining a codon position of a proposed frameshift group; and conditionally categorizing the second gene variant as a member of the proposed frameshift group if the codon position of the second gene variant is equal to the codon position of the frameshift group.

(29) At least one non-transitory computer-readable storage medium storing processor-executable instructions that, when executed by at least one processor, cause the at least one processor to perform a method for determining relationships between gene variants of a gene, the gene variants being related to one or more cancers and being correlated to a treatment response of the one or more cancers to one or more medications, the method comprising: accessing a database comprising information about the gene variants, the information including at least information indicative of a treatment response of a first gene variant of the gene variants to one or more treatments; categorizing the information about the gene variants within a plurality of groups; and generating hierarchical relationships between each group of the plurality of groups.

(30) The at least one non-transitory computer-readable storage medium of (29), further comprising: generating, using the at least one processor, a visualization of the hierarchical relationships between each group of the plurality of groups; and displaying, on a user interface of a computing device, the visualization.

(31) The at least one non-transitory computer-readable storage medium of any one of (29)-(30), wherein the act of categorizing further comprises categorizing the information about the gene variants within the plurality of groups such that each member of a group of the plurality of groups is unique.

(32) The at least one non-transitory computer-readable storage medium of any one of (29)-(31), wherein categorizing further comprises selecting, based on the categorized information about the gene variants within a group of the plurality of groups, an owner member of the group, wherein the owner member comprises information about a group category.

(33) The at least one non-transitory computer-readable storage medium of any one of (29)-(32), wherein the act of generating the hierarchical relationship further comprises generating a directed acyclic graph.

(34) The at least one non-transitory computer-readable storage medium of any one of (29)-(33), wherein categorizing, using the at least one processor, the information about the gene variants further comprises: determining, based on information associated with a second gene variant of the gene variants, whether the second gene variant is a specific fusion mutation; and conditionally categorizing, based on determining that the second gene variant is a specific fusion mutation, the second gene variant as a member of a fusion group or a rearrange group by determining whether the information associated with the second gene variant includes information indicating that a gene group including the second gene variant includes a fusion group or a rearrange group.

(35) The at least one non-transitory computer-readable storage medium of any one of (29)-(34), wherein categorizing, using the at least one processor, the information about the gene variants further comprises: determining, based on information associated with a second gene variant of the gene variants, whether the second gene variant is a fusion mutation; and conditionally categorizing, based on determining that the second gene variant is a fusion mutation, the second gene variant as a member of a rearrange group by determining whether the information associated with the second gene variant includes information indicating that a gene group including the second gene variant includes a rearrange group.

(36) The at least one non-transitory computer-readable storage medium of any one of (29)-(35), wherein categorizing, using the at least one processor, the information about the gene variants further comprises: determining, based on information associated with a second gene variant of the gene variants, whether the second gene variant is a non-specific mutation type; determining, based on the information associated with the second gene variant, whether the second gene variant is a mutant; determining whether the information associated with the second gene variant includes information indicating that a gene group including the second gene variant includes a mutant group; and conditionally categorizing the second gene variant as a member of a mutant group if: (1) the second gene variant is not a non-specific mutation type, (2) the second gene variant is not a mutant, and (3) the information associated with the second gene variant includes information indicating that a gene group including the second gene variant includes a mutant group.

(37) The at least one non-transitory computer-readable storage medium of any one of (29)-(36), wherein categorizing, using the at least one processor, the information about the gene variants further comprises: determining, based on information associated with a second gene variant of the gene variants, whether the second gene variant is a gene variant having an activating protein effect; determining whether the information associated with the second gene variant includes information indicating that a gene group including the second gene variant includes an activating mutation (act mut) group; and conditionally categorizing the second gene variant as a member of an act mut group if: (1) the second gene variant is a gene variant having an activating protein effect and (2) the information associated with the second gene variant includes information indicating that a gene group including the second gene variant includes an act mut group.

(38) The at least one non-transitory computer-readable storage medium of any one of (29)-(37), wherein categorizing, using the at least one processor, the information about the gene variants further comprises: determining, based on information associated with a second gene variant of the gene variants, whether the second gene variant is a gene variant having an inactivating protein effect; determining whether the information associated with the second gene variant includes information indicating that a gene group including the second gene variant includes an inactivating mutation (inact mut) group; and conditionally categorizing the second gene variant as a member of an inact mut group if: (1) the second gene variant is a gene variant having an inactivating protein effect and (2) the information associated with the second gene variant includes information indicating that a gene group including the second gene variant includes an inact mut group.

(39) The at least one non-transitory computer-readable storage medium of any one of (29)-(38), wherein categorizing, using the at least one processor, the information about the gene variants further comprises: determining, based on information associated with a second gene variant of the gene variants, whether the second gene variant is a positional mutation; determining a codon position of the second gene variant based on the information associated with the second gene variant; comparing the determined codon position of the second gene variant with a codon position of a proposed positional group; and conditionally categorizing the second gene variant as a member of the positional group if the determined codon position of the second gene variant is equal to the codon position of the proposed positional group.

(40) The at least one non-transitory computer-readable storage medium of any one of (29)-(39), wherein categorizing, using the at least one processor, the information about the gene variants further comprises: determining whether a second gene variant is a V600E or V600K gene variant based on information associated with the second gene variant; determining whether the information associated with the second gene variant includes information indicating that a gene group including the second gene variant includes a V600E or V600K group; conditionally categorizing the second gene variant as a member of a V600E or V600K group if: (1) the second gene variant is a V600E or V600K gene variant and (2) the information associated with the second gene variant includes information indicating that a gene group including the second gene variant includes a V600E or V600K group.

(41) The at least one non-transitory computer-readable storage medium of any one of (29)-(40), wherein categorizing, using the at least one processor, the information about the gene variants further comprises: determining, based on information associated with a second gene variant of the gene variants, whether the second gene variant is a part of a gene-exon map; (1) conditionally determining, based on the determination that the second gene variant is a part of the gene-exon map and the information associated with the second gene variant, if a codon position of the second gene variant is within a positional range of an exon in the gene-exon map; (2) conditionally determining, based on the determination that the second gene variant is a part of the gene-exon map, if the information associated with the second gene variant comprises information indicative of the second gene variant belonging to an exon #indel group; and conditionally categorizing, based on affirmative determinations in (1) and/or (2), the second gene variant as a member of an exon group and/or an exon indel group.

(42) The at least one non-transitory computer-readable storage medium of any one of (29)-(41), wherein categorizing, using the at least one processor, the information about the gene variants further comprises: determining, based on information associated with a second gene variant, whether a second gene variant of the gene variants is a frameshift gene variant; determining, based on the information associated with the second gene variant, a codon position of a second gene variant; determining a codon position of a proposed frameshift group; and conditionally categorizing the second gene variant as a member of the proposed frameshift group if the codon position of the second gene variant is equal to the codon position of the frameshift group.

(43) A method of treating a patient, the patient having a cancer with a gene variant, the method comprising: accessing, using at least one processor, a database comprising information about gene variants associated with cancers, the information including at least information indicative of a treatment response of a first gene variant of the gene variants to one or more treatments; categorizing, using the at least one processor, the information about the gene variants within a plurality of groups; generating, using the at least one processor, hierarchical relationships between each group of the plurality of groups; determining, using the hierarchical relationships between each group and the information indicative of a treatment response of a first gene variant, a treatment modality correlated with the gene variant; and treating the patient using the treatment modality.

What is claimed is:

1. A method for determining relationships between gene variants of a gene, the gene variants being related to one or more cancers and being correlated to a treatment response of the one or more cancers to one or more treatments, the method comprising:

accessing, using at least one processor, a database comprising information about the gene variants, the information including at least information indicative of a treatment response of a first gene variant of the gene variants to one or more treatments;

categorizing, using the at least one processor, the information about the gene variants within a plurality of groups by:

determining, based on the information about the gene variants, one or more attributes of respective mutations associated with the gene variants;

determining whether the information about the gene variants includes (1) information indicating a gene group, the gene group including a particular gene variant and (2) information indicating the gene group includes a particular group of the plurality of groups associated with an attribute of the particular gene variant; and categorizing the gene variants within the plurality of groups based on determining the information indicates the determined one or more attributes and, each of the plurality of groups associated with an attribute of respective mutations associated with the gene variants;

generating, using the at least one processor, hierarchical relationships between each group of the plurality of groups, wherein the hierarchical relationships form a directed acyclic graph, the hierarchical relationships between each group indicating relationships between the attributes of respective mutations associated with the gene variants;

generating, using the at least one processor, a visualization of the hierarchical relationships between each group of the plurality of groups; and displaying, on a user interface of a computing device, the visualization.

2. The method of claim 1, wherein the act of categorizing further comprises categorizing the information about the gene variants within the plurality of groups such that each member of a group of the plurality of groups is unique.

3. The method of claim 1, wherein categorizing further comprises:

selecting, based on the categorized information about the gene variants within a group of the plurality of groups, an owner member of the group, wherein the owner member comprises information about a group category.

4. The method of claim 1, wherein categorizing, using the at least one processor, the information about the gene variants further comprises:

determining, based on information associated with a second gene variant of the gene variants, whether the second gene variant is a specific fusion mutation; and conditionally categorizing, based on determining that the second gene variant is a specific fusion mutation, the second gene variant as a member of a fusion group or a rearrange group by determining whether the information associated with the second gene variant includes information indicating that a gene group including the second gene variant includes a fusion group or a rearrange group.

5. The method of claim 1, wherein categorizing, using the at least one processor, the information about the gene variants further comprises:

determining, based on information associated with a second gene variant of the gene variants, whether the second gene variant is a fusion mutation; and conditionally categorizing, based on determining that the second gene variant is a fusion mutation, the second gene variant as a member of a rearrange group by determining whether the information associated with the second gene variant includes information indicating that a gene group including the second gene variant includes a rearrange group.

6. The method of claim 1, wherein categorizing, using the at least one processor, the information about the gene variants further comprises:

determining, based on information associated with a second gene variant of the gene variants, whether the second gene variant is a non-specific mutation type;

determining, based on the information associated with the second gene variant, whether the second gene variant is a mutant;

determining whether the information associated with the second gene variant includes information indicating that a gene group including the second gene variant includes a mutant group; and conditionally categorizing the second gene variant as a member of a mutant group if: (1) the second gene variant is not a non-specific mutation type, (2) the second gene variant is not a mutant, and (3) the information associated with the second gene variant includes information indicating that a gene group including the second gene variant includes a mutant group.

7. The method of claim 1, wherein categorizing, using the at least one processor, the information about the gene variants further comprises:

determining, based on information associated with a second gene variant of the gene variants, whether the second gene variant is a gene variant having an activating protein effect;

determining whether the information associated with the second gene variant includes information indicating that a gene group including the second gene variant includes an activating mutation (act mut) group; and conditionally categorizing the second gene variant as a member of an act mut group if: (1) the second gene variant is a gene variant having an activating protein effect and (2) the information associated with the second gene variant includes information indicating that a gene group including the second gene variant includes an act mut group.

8. The method of claim 1, wherein categorizing, using the at least one processor, the information about the gene variants further comprises:

determining, based on information associated with a second gene variant of the gene variants, whether the second gene variant is a gene variant having an inactivating protein effect;

determining whether the information associated with the second gene variant includes information indicating that a gene group including the second gene variant includes an inactivating mutation (inact mut) group; and conditionally categorizing the second gene variant as a member of an inact mut group if: (1) the second gene variant is a gene variant having an inactivating protein effect and (2) the information associated with the second gene variant includes information indicating that a gene group including the second gene variant includes an inact mut group.

9. The method of claim 1, wherein categorizing, using the at least one processor, the information about the gene variants further comprises:

determining, based on information associated with a second gene variant of the gene variants, whether the second gene variant is a positional mutation;

determining a codon position of the second gene variant based on the information associated with the second gene variant;

comparing the determined codon position of the second gene variant with a codon position of a proposed positional group; and conditionally categorizing the second gene variant as a member of the proposed positional group if the determined codon position of the second gene variant is equal to the codon position of the proposed positional group.

10. The method of claim 1, wherein categorizing, using the at least one processor, the information about the gene variants further comprises:

determining whether a second gene variant is a V600E or V600K gene variant based on information associated with the second gene variant;

determining whether the information associated with the second gene variant includes information indicating that a gene group including the second gene variant includes a V600E or V600K group; and conditionally categorizing the second gene variant as a member of a V600E or V600K group if: (1) the second gene variant is a V600E or V600K gene variant and (2) the information associated with the second gene variant includes information indicating that a gene group including the second gene variant includes a V600E or V600K group.

11. The method of claim 1, wherein categorizing, using the at least one processor, the information about the gene variants further comprises:

determining, based on information associated with a second gene variant of the gene variants, whether the second gene variant is a part of a gene-exon map;

(1) conditionally determining, based on the determination that the second gene variant is a part of the gene-exon map and the information associated with the second gene variant, if a codon position of the second gene variant is within a positional range of an exon in the gene-exon map;

(2) conditionally determining, based on the determination that the second gene variant is a part of the gene-exon map, if the information associated with the second gene variant comprises information indicative of the second gene variant belonging to an exon #indel group; and conditionally categorizing, based on affirmative determinations in (1) and/or (2), the second gene variant as a member of an exon group and/or an exon indel group.

12. The method of claim 1, wherein categorizing, using the at least one processor, the information about the gene variants further comprises:

determining, based on information associated with a second gene variant, whether a second gene variant of the gene variants is a frameshift gene variant;

determining, based on the information associated with the second gene variant, a codon position of a second gene variant;

determining a codon position of a proposed frameshift group; and conditionally categorizing the second gene variant as a member of the proposed frameshift group if the codon position of the second gene variant is equal to the codon position of the proposed frameshift group.

13. A system for determining relationships between gene variants of a gene, the gene variants being related to one or more cancers and being correlated to a treatment response of the one or more cancers to one or more medications, the system comprising:

at least one processor; and at least one computer memory storing instructions, that, when executed by the at least one processor, perform a method of:

accessing, using at least one processor, a database comprising information about the gene variants, the information including at least information indicative of a treatment response of a first gene variant of the gene variants to one or more treatments;

categorizing, using the at least one processor, the information about the gene variants within a plurality of groups by:

determining, based on the information about the gene variants, one or more attributes of respective mutations associated with the gene variants;

determining whether the information about the gene variants includes (1) information indicating a gene group, the gene group including a particular gene variant and (2) information indicating the gene group includes a particular group of the plurality of groups associated with an attribute of the particular gene variant; and categorizing the gene variants within the plurality of groups based on determining the information indicates the determined one or more attributes and, each of the plurality of groups associated with an attribute of respective mutations associated with the gene variants;

generating, using the at least one processor, hierarchical relationships between each group of the plurality of groups, wherein the hierarchical relationships form a directed acyclic graph, the hierarchical relationships between each group indicating relationships between the attributes of respective mutations associated with the gene variants;

generating, using the at least one processor, a visualization of the hierarchical relationships between each group of the plurality of groups; and displaying, on a user interface of a computing device, the visualization.

14. The system of claim 13, wherein the act of categorizing further comprises categorizing the information about the gene variants within the plurality of groups such that each member of a group of the plurality of groups is unique.

15. The system of claim 13, wherein categorizing further comprises:

selecting, based on the categorized information about the gene variants within a group of the plurality of groups, an owner member of the group, wherein the owner member comprises information about a group category.

16. The system of claim 13, wherein categorizing, using the at least one processor, the information about the gene variants further comprises:

determining, based on information associated with a second gene variant of the gene variants, whether the second gene variant is a specific fusion mutation; and conditionally categorizing, based on determining that the second gene variant is a specific fusion mutation, the second gene variant as a member of a fusion group or a rearrange group by determining whether the information associated with the second gene variant includes information indicating that a gene group including the second gene variant includes a fusion group or a rearrange group.

17. The system of claim 13, wherein categorizing, using the at least one processor, the information about the gene variants further comprises:

determining, based on information associated with a second gene variant of the gene variants, whether the second gene variant is a fusion mutation; and conditionally categorizing, based on determining that the second gene variant is a fusion mutation, the second gene variant as a member of a rearrange group by determining whether the information associated with the second gene variant includes information indicating that a gene group including the second gene variant includes a rearrange group.

18. At least one non-transitory computer-readable storage medium storing processor-executable instructions that, when executed by at least one processor, cause the at least one processor to perform a method for determining relationships between gene variants of a gene, the gene variants being related to one or more cancers and being correlated to a treatment response of the one or more cancers to one or more medications, the method comprising:

accessing a database comprising information about the gene variants, the information including at least information indicative of a treatment response of a first gene variant of the gene variants to one or more treatments;

categorizing the information about the gene variants within a plurality of groups by:

determining, based on the information about the gene variants, one or more attributes of respective mutations associated with the gene variants;

determining whether the information about the gene variants includes (1) information indicating a gene group, the gene group including a particular gene variant and (2) information indicating the gene group includes a particular group of the plurality of groups associated with an attribute of the particular gene variant; and categorizing the gene variants within the plurality of groups based on determining the information indicates the determined one or more attributes and, each of the plurality of groups associated with an attribute of respective mutations associated with the gene variants;

generating hierarchical relationships between each group of the plurality of groups, wherein the hierarchical relationships form a directed acyclic graph, the hierarchical relationships between each group indicating relationships between the attributes of respective mutations associated with the gene variants;

generating, using the at least one processor, a visualization of the hierarchical relationships between each group of the plurality of groups; and displaying, on a user interface of a computing device, the visualization.

* * * * *